United States Patent
Wada et al.

(10) Patent No.: US 8,697,655 B2
(45) Date of Patent: Apr. 15, 2014

(54) METHOD OF SELECTING POLYPEPTIDE SEQUENCE, AND METAL OXIDE OR SILICON-CONTAINING COMPOUND BINDING PEPTIDE AND USE THEREOF

(75) Inventors: Akira Wada, Wako (JP); Yoshihiro Ito, Wako (JP); Takashi Kitajima, Wako (JP)

(73) Assignee: Riken, Saitama (JP)

( * ) Notice: Subject to any disclaimer, the term of this patent is extended or adjusted under 35 U.S.C. 154(b) by 0 days.

(21) Appl. No.: 13/608,052

(22) Filed: Sep. 10, 2012

(65) Prior Publication Data

US 2013/0045917 A1 Feb. 21, 2013

Related U.S. Application Data

(63) Continuation-in-part of application No. PCT/JP2011/055815, filed on Mar. 11, 2011.

(30) Foreign Application Priority Data

Mar. 11, 2010 (JP) .................. 2010-054927

(51) Int. Cl.
| | |
|---|---|
| A61K 38/10 | (2006.01) |
| C12N 15/00 | (2006.01) |
| C07H 21/04 | (2006.01) |
| A61K 38/00 | (2006.01) |
| C07K 1/00 | (2006.01) |
| A61K 38/24 | (2006.01) |

(52) U.S. Cl.
USPC ..... 514/21.4; 435/320.1; 536/23.5; 536/23.4; 530/326; 530/402; 530/399

(58) Field of Classification Search
None
See application file for complete search history.

(56) References Cited

U.S. PATENT DOCUMENTS

| | | | |
|---|---|---|---|
| 5,643,768 A | 7/1997 | Kawasaki | |
| 5,658,754 A | 8/1997 | Kawasaki | |
| 6,348,315 B1 | 2/2002 | Pluckthun et al. | |
| 6,589,741 B2 | 7/2003 | Pluckthun et al. | |
| 6,620,587 B1 | 9/2003 | Taussig et al. | |
| 7,256,038 B2 * | 8/2007 | Daugherty et al. | ........ 435/320.1 |
| 7,498,403 B2 * | 3/2009 | Shiba et al. | .................. 530/327 |
| 7,972,615 B2 * | 7/2011 | Orgambide et al. | .......... 424/422 |
| 2002/0115083 A1 | 8/2002 | Pluckthun et al. | |
| 2009/0023602 A1 | 1/2009 | Fellouse et al. | |

FOREIGN PATENT DOCUMENTS

| | | |
|---|---|---|
| JP | 3127158 B2 | 11/2000 |
| JP | 2001-521395 A | 11/2001 |
| JP | 2002-500514 A | 1/2002 |
| JP | 2009-136280 A | 6/2005 |
| JP | 2007-501011 A | 1/2007 |
| JP | 2007-029061 A | 2/2007 |
| WO | 01/75097 A2 | 10/2001 |

OTHER PUBLICATIONS

"Capsular exopolysaccharide family protein", [online], UniProt, Mar. 2, 2010, AC: B6BT02, [retrieval date May 17, 2011], <URL, http://www.uniprot.org/uniprot/B6BT02.txt?version=10>.

Mersich et al., "Generation of Bioactive Peptides by Biological Libraries" *Journal of Chromatography B*, 861 (2) : 160-70, published online Jul. 3, 2007.

Chen et al., "Selection of IgE-Binding Aptameric Green Fluorescent Protein (Ap-GFP) by the Ribosome Display (RD) Platform" *Biochem. Biophys. Res. Comm.*, 374(3):409-14, published online Jul. 9, 2008.

Sano et al., "Specificity and Biomineralization Activities of Ti-Binding Peptide-1 (TBP-1)" *Langmuir*, 21:3090-95, published online Feb. 23, 2005.

Hayashi et al., "Mechanism Underlying Specificity of Proteins Targeting Inorganic Meterials" *Nano Lett.*, 6(3):515-19, published online Feb. 18, 2006.

International Preliminary Report on Patentability for PCT/JP2011/055815, mailed Oct. 11, 2012.

International Search Report for PCT/JP2011/055815, mailed May 31, 2011.

\* cited by examiner

*Primary Examiner* — Shulamith H Shafer

(74) *Attorney, Agent, or Firm* — Greenblum & Bernstein, P.L.C.

(57) ABSTRACT

Provided is a peptide including the following amino acid sequence. Tyr-$Xaa^0$-$Xaa^1$-Tyr-Tyr-$Xaa^2$-$Xaa^3$-Tyr-$Xaa^4$-$Xaa^5$-$Xaa^6$-$Xaa^7$-$Xaa^8$-$Xaa^9$-$Xaa^{10}$-$Xaa^{11}$ (SEQ ID NO: 4: wherein $Xaa^0$, $Xaa^1$, $Xaa^2$, $Xaa^3$, $Xaa^4$, $Xaa^5$, $Xaa^6$, $Xaa^7$, $Xaa^8$, $Xaa^9$, $Xaa^{10}$ and $Xaa^{11}$ represent any amino acid) or Tyr-Asn-Asp-Tyr-Tyr-Tyr-Tyr-Cys-Tyr-Arg-Asp-Tyr-Asp (SEQ ID NO: 20).

21 Claims, 4 Drawing Sheets

Fig. 1

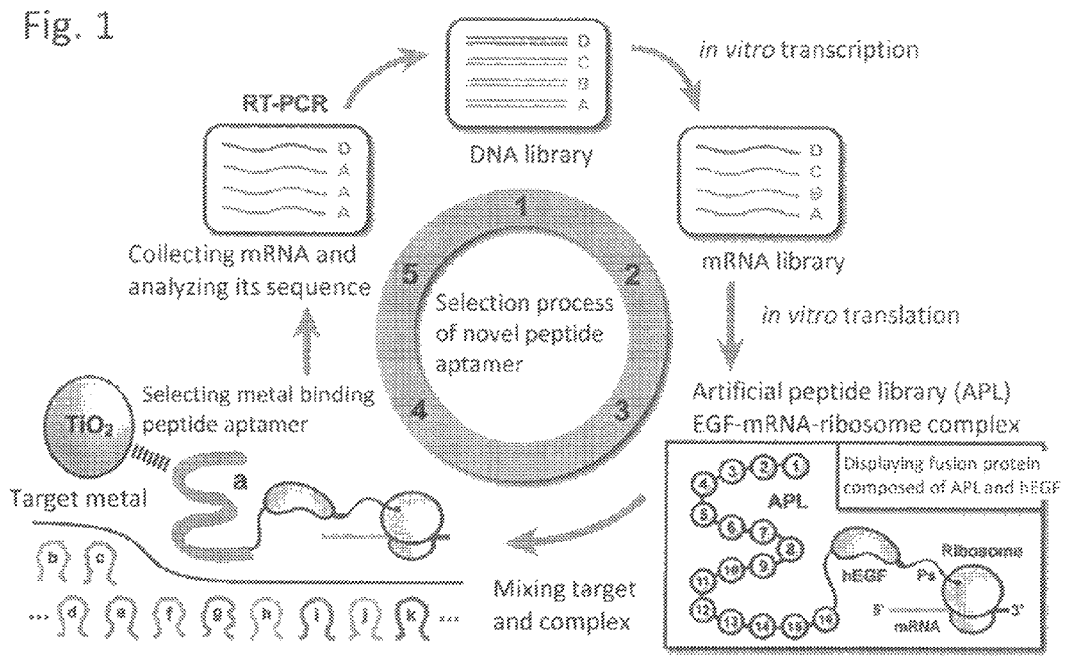

Fig. 2

1. Novel design of DNA template

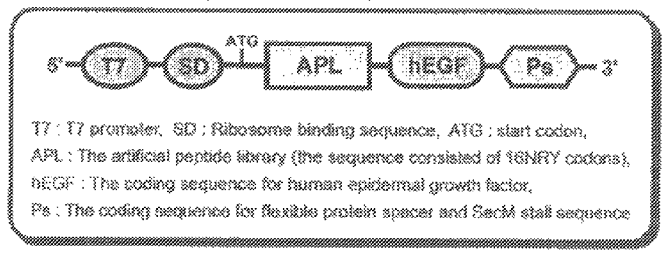

T7 : T7 promoter, SD : Ribosome binding sequence, ATG : start codon,
APL : The artificial peptide library (the sequence consisted of 16NRY codons),
hEGF : The coding sequence for human epidermal growth factor,
Ps : The coding sequence for flexible protein spacer and SecM stall sequence 2. DNA template sequence for using in ribosome display method    SEQ ID NO: 1

T7                                                               SD           start codon
TTAATACGACTCACTATAGAAAAGTCGACAATAATTTTGTTTAACTTTAAGAAGGAGATATACATATGGCCATGCAG
GCCNRYNRYNRYNRYNRYNRYNRYNRYNRYNRYNRYNRYNRYNRYNRYNRYGGCCAGCTAGGCCAGTTCGAAGGTAA
TAGTGACTCTGAATGTCCCCTGTCCCACGATGGGTACTGCCTCCATGATGGTGTGTGCATGTATATTGAAGCATTGG
ACAAGTATGCATGCAACTGTGTTGTTGGCTACATCGGGGAGCGATGTCAGTACCGAGACCTGAAGTGGTGGGAACTG
CGCTTCGAATCTGATGTTGAAGAGAATCGCACTGAAGCTCCAGAAGGTACCGAGTCTGAAATGGAAACACCATCGGC
CATCAACGGTAATCCGTCGTGGCACCTGGCCGATAGCCCAGCTGTGAATGGTGCTACTGGAGGTTCGAGCTCTGACG
TTGAAGAGAACCGCACCGAGGCACCAGAAGGAACCGAATCCGAAATGGAGACACCGTCTGCTATCAACGGCAATCCA
TCGTGGCACCTCGCTGACTCTCCAGCCGTCAATGGAGCTACCGGGATCCAGTTTTCTACTCCTGTTTGGATTTCTCA
AGCTCAAGGTATTCGTGCTGGTCCTCAACGTCTCACTCAGCTTGGCGTAATCATGGTCATAGCTGTTT Fig. 3
1. Sequences of various peptide fusion EGFs (P-EGFs)
2. Expression of P-EGFs by cell free protein translation system
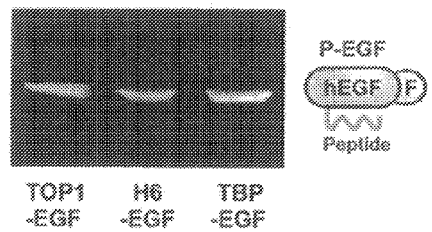
Fig. 4
1. Evaluation of binding ability of peptide fusion EGFs to surface of $TiO_2$ particles
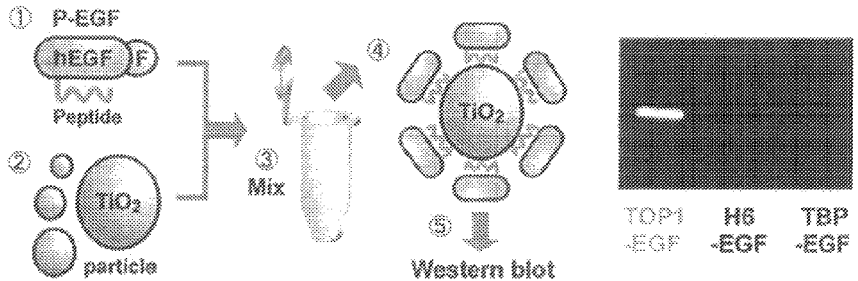
2. Evaluation of binding ability of peptide fusion EGFs to surface of $TiO_2$ plate
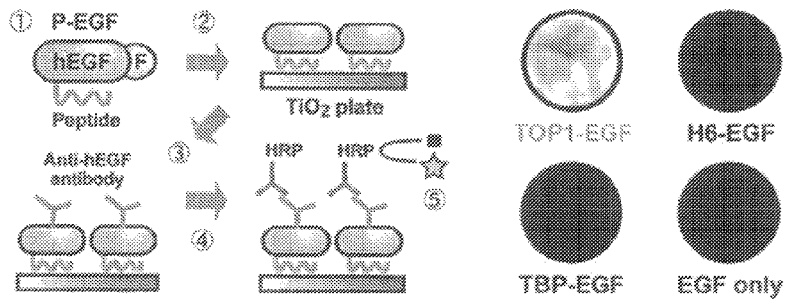

Fig. 5
Evaluation of binding ability of peptide fusion EGFs to surface of TiO$_2$ plate
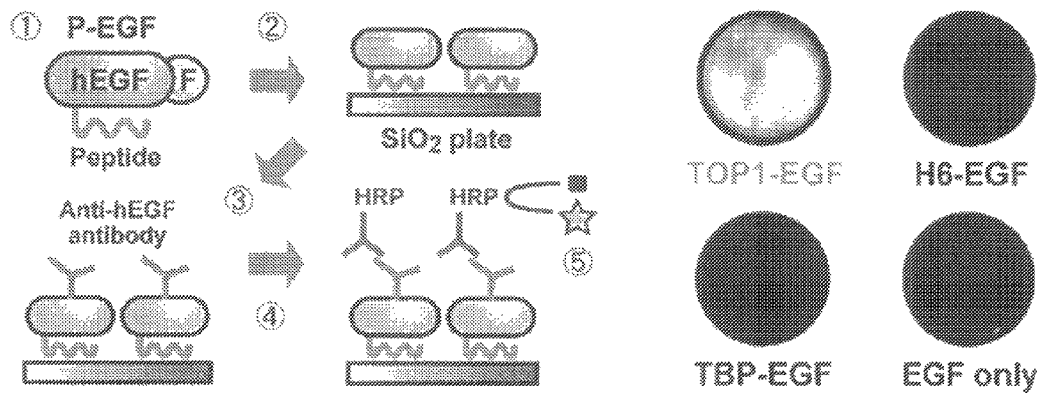
Fig. 6
1. Evaluation of cell proliferation activity of peptide fusion EGFs on surface of TiO$_2$ plate
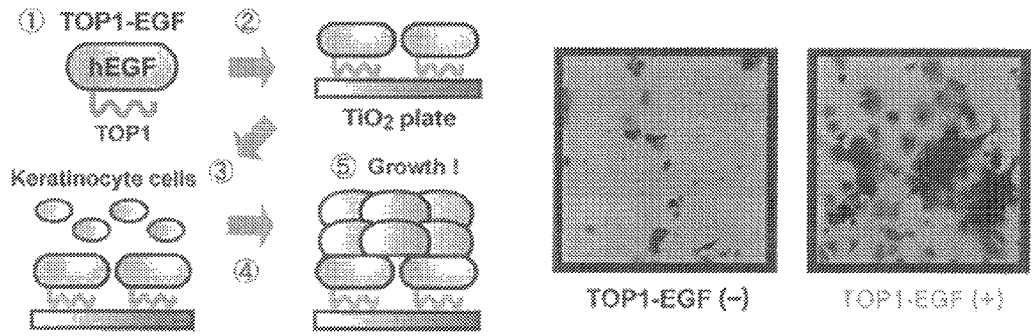
2. Evaluation of cell proliferation activity of peptide fusion EGFs on surface of TiO$_2$ plate
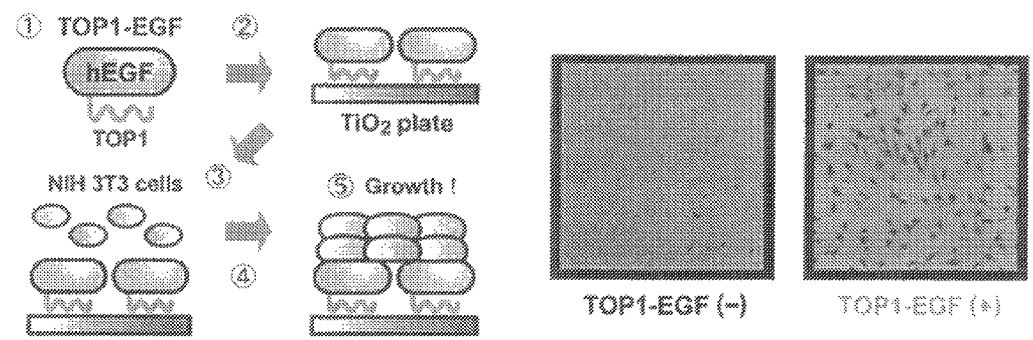

Fig. 7
1. Evaluation of binding ability of peptide fusion EGFs to surface of $TiO_2$ plates
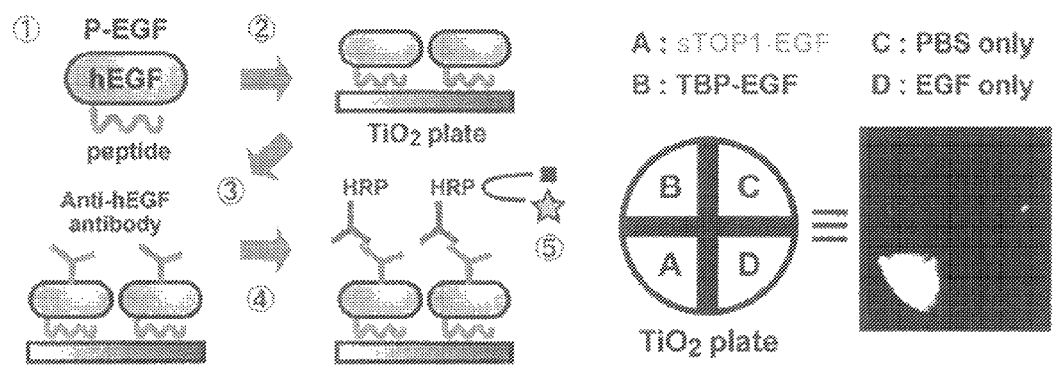
2. Evaluation of cell proliferation activity of peptide fusion EGFs on surface of $TiO_2$ plate
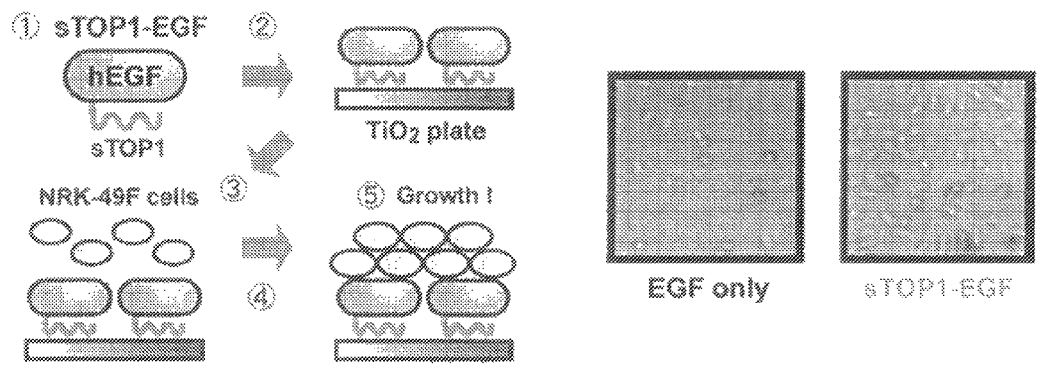

SEQUENCE LISTING

```
<160> NUMBER OF SEQ ID NOS: 23

<210> SEQ ID NO 1
<211> LENGTH: 684
<212> TYPE: DNA
<213> ORGANISM: Artificial Sequence
<220> FEATURE:
<223> OTHER INFORMATION: Description of Artificial Sequence: Synthetic
      DNA construct sequence
<220> FEATURE:
<221> NAME/KEY: CDS
<222> LOCATION: (66)..(683)
<220> FEATURE:
<221> NAME/KEY: modified_base
<222> LOCATION: (81)..(81)
<223> OTHER INFORMATION: a, c, t, g, unknown or other
<220> FEATURE:
<221> NAME/KEY: modified_base
<222> LOCATION: (84)..(84)
<223> OTHER INFORMATION: a, c, t, g, unknown or other
<220> FEATURE:
<221> NAME/KEY: modified_base
<222> LOCATION: (87)..(87)
<223> OTHER INFORMATION: a, c, t, g, unknown or other
<220> FEATURE:
<221> NAME/KEY: modified_base
<222> LOCATION: (90)..(90)
<223> OTHER INFORMATION: a, c, t, g, unknown or other
<220> FEATURE:
<221> NAME/KEY: modified_base
<222> LOCATION: (93)..(93)
<223> OTHER INFORMATION: a, c, t, g, unknown or other
<220> FEATURE:
<221> NAME/KEY: modified_base
<222> LOCATION: (96)..(96)
<223> OTHER INFORMATION: a, c, t, g, unknown or other
<220> FEATURE:
<221> NAME/KEY: modified_base
<222> LOCATION: (99)..(99)
<223> OTHER INFORMATION: a, c, t, g, unknown or other
<220> FEATURE:
<221> NAME/KEY: modified_base
<222> LOCATION: (102)..(102)
<223> OTHER INFORMATION: a, c, t, g, unknown or other
<220> FEATURE:
<221> NAME/KEY: modified_base
<222> LOCATION: (105)..(105)
<223> OTHER INFORMATION: a, c, t, g, unknown or other
<220> FEATURE:
<221> NAME/KEY: modified_base
<222> LOCATION: (108)..(108)
<223> OTHER INFORMATION: a, c, t, g, unknown or other
<220> FEATURE:
<221> NAME/KEY: modified_base
<222> LOCATION: (111)..(111)
<223> OTHER INFORMATION: a, c, t, g, unknown or other
```

```
<220> FEATURE:
<221> NAME/KEY: modified_base
<222> LOCATION: (114)..(114)
<223> OTHER INFORMATION: a, c, t, g, unknown or other
<220> FEATURE:
<221> NAME/KEY: modified_base
<222> LOCATION: (117)..(117)
<223> OTHER INFORMATION: a, c, t, g, unknown or other
<220> FEATURE:
<221> NAME/KEY: modified_base
<222> LOCATION: (120)..(120)
<223> OTHER INFORMATION: a, c, t, g, unknown or other
<220> FEATURE:
<221> NAME/KEY: modified_base
<222> LOCATION: (123)..(123)
<223> OTHER INFORMATION: a, c, t, g, unknown or other
<220> FEATURE:
<221> NAME/KEY: modified_base
<222> LOCATION: (126)..(126)
<223> OTHER INFORMATION: a, c, t, g, unknown or other

<400> SEQUENCE: 1
ttaatacgac tcactataga aaagtcgaca ataattttgt ttaactttaa gaaggagata      60 tacat atg gcc atg cag gcc nry nry nry nry nry nry nry nry nry         110
      Met Ala Met Gln Ala Xaa Xaa Xaa Xaa Xaa Xaa Xaa Xaa Xaa
      1               5                  10                  15 nry nry nry nry nry nry ggc cag cta ggc cag ttc gaa ggt aat agt       158
Xaa Xaa Xaa Xaa Xaa Xaa Gly Gln Leu Gly Gln Phe Glu Gly Asn Ser
                20                  25                  30 gac tct gaa tgt ccc ctg tcc cac gat ggg tac tgc ctc cat gat ggt       206
Asp Ser Glu Cys Pro Leu Ser His Asp Gly Tyr Cys Leu His Asp Gly
                35                  40                  45 gtg tgc atg tat att gaa gca ttg gac aag tat gca tgc aac tgt gtt       254
Val Cys Met Tyr Ile Glu Ala Leu Asp Lys Tyr Ala Cys Asn Cys Val
            50                  55                  60 gtt ggc tac atc ggg gag cga tgt cag tac cga gac ctg aag tgg tgg       302
Val Gly Tyr Ile Gly Glu Arg Cys Gln Tyr Arg Asp Leu Lys Trp Trp
        65                  70                  75 gaa ctg cgc ttc gaa tct gat gtt gaa gag aat cgc act gaa gct cca       350
Glu Leu Arg Phe Glu Ser Asp Val Glu Glu Asn Arg Thr Glu Ala Pro
80                  85                  90                  95 gaa ggt acc gag tct gaa atg gaa aca cca tcg gcc atc aac ggt aat       398
Glu Gly Thr Glu Ser Glu Met Glu Thr Pro Ser Ala Ile Asn Gly Asn
                100                 105                 110 ccg tcg tgg cac ctg gcc gat agc cca gct gtg aat ggt gct act gga       446
Pro Ser Trp His Leu Ala Asp Ser Pro Ala Val Asn Gly Ala Thr Gly
            115                 120                 125 ggt tcg agc tct gac gtt gaa gag aac cgc acc gag gca cca gaa gga       494
Gly Ser Ser Ser Asp Val Glu Glu Asn Arg Thr Glu Ala Pro Glu Gly
        130                 135                 140 acc gaa tcc gaa atg gag aca ccg tct gct atc aac ggc aat cca tcg       542
Thr Glu Ser Glu Met Glu Thr Pro Ser Ala Ile Asn Gly Asn Pro Ser
            145                 150                 155 tgg cac ctc gct gac tct cca gcc gtc aat gga gct acc ggg atc cag       590
Trp His Leu Ala Asp Ser Pro Ala Val Asn Gly Ala Thr Gly Ile Gln
160                 165                 170                 175 ttt tct act cct gtt tgg att tct caa gct caa ggt att cgt gct ggt       638
Phe Ser Thr Pro Val Trp Ile Ser Gln Ala Gln Gly Ile Arg Ala Gly
                180                 185                 190 cct caa cgt ctc act cag ctt ggc gta atc atg gtc ata gct gtt t         684
Pro Gln Arg Leu Thr Gln Leu Gly Val Ile Met Val Ile Ala Val
            195                 200                 205
```

-continued

```
<210> SEQ ID NO 2
<211> LENGTH: 206
<212> TYPE: PRT
<213> ORGANISM: Artificial Sequence
<220> FEATURE:
<223> OTHER INFORMATION: Description of Artificial Sequence: Synthetic
      construct sequence
<220> FEATURE:
<221> NAME/KEY: misc_feature
<222> LOCATION: (6)..(21)
<223> OTHER INFORMATION: Ser, Asn, Gly, Asp, Arg, His, Cys, or Tyr

<400> SEQUENCE: 2
```

Met Ala Met Gln Ala Xaa Xaa Xaa Xaa Xaa Xaa Xaa Xaa Xaa Xaa
1               5                   10                  15

Xaa Xaa Xaa Xaa Xaa Gly Gln Leu Gly Gln Phe Glu Gly Asn Ser Asp
                20                  25                  30

Ser Glu Cys Pro Leu Ser His Asp Gly Tyr Cys Leu His Asp Gly Val
            35                  40                  45

Cys Met Tyr Ile Glu Ala Leu Asp Lys Tyr Ala Cys Asn Cys Val Val
    50                  55                  60

Gly Tyr Ile Gly Glu Arg Cys Gln Tyr Arg Asp Leu Lys Trp Trp Glu
65                  70                  75                  80

Leu Arg Phe Glu Ser Asp Val Glu Glu Asn Arg Thr Glu Ala Pro Glu
                85                  90                  95

Gly Thr Glu Ser Glu Met Glu Thr Pro Ser Ala Ile Asn Gly Asn Pro
            100                 105                 110

Ser Trp His Leu Ala Asp Ser Pro Ala Val Asn Gly Ala Thr Gly Gly
        115                 120                 125

Ser Ser Ser Asp Val Glu Glu Asn Arg Thr Glu Ala Pro Glu Gly Thr
    130                 135                 140

Glu Ser Glu Met Glu Thr Pro Ser Ala Ile Asn Gly Asn Pro Ser Trp
145                 150                 155                 160

His Leu Ala Asp Ser Pro Ala Val Asn Gly Ala Thr Gly Ile Gln Phe
                165                 170                 175

Ser Thr Pro Val Trp Ile Ser Gln Ala Gln Gly Ile Arg Ala Gly Pro
            180                 185                 190

Gln Arg Leu Thr Gln Leu Gly Val Ile Met Val Ile Ala Val
        195                 200                 205

```
<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: secM
<220> FEATURE:
<221> NAME/KEY: MOD_RES
<222> LOCATION: (2)..(5)
<223> OTHER INFORMATION: Any amino acid
<220> FEATURE:
<221> NAME/KEY: MOD_RES
<222> LOCATION: (8)..(11)
<223> OTHER INFORMATION: Any amino acid

<400> SEQUENCE: 3
```

Phe Xaa Xaa Xaa Xaa Trp Ile Xaa Xaa Xaa Xaa Gly Ile Arg Ala Gly
1               5                   10                  15

Pro

```
<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: TiO2 and SiO2 binding peptide
<220> FEATURE:
<221> NAME/KEY: MOD_RES
<222> LOCATION: (2)..(3)
<223> OTHER INFORMATION: Any amino acid
<220> FEATURE:
<221> NAME/KEY: MOD_RES
<222> LOCATION: (6)..(7)
<223> OTHER INFORMATION: Any amino acid
<220> FEATURE:
<221> NAME/KEY: MOD_RES
<222> LOCATION: (9)..(16)
<223> OTHER INFORMATION: Any amino acid

<400> SEQUENCE: 4

Tyr Xaa Xaa Tyr Tyr Xaa Xaa Tyr Xaa Xaa Xaa Xaa Xaa Xaa Xaa Xaa
1               5                   10                  15

<210> SEQ ID NO 5
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: TOP1
<220> FEATURE:
<221> NAME/KEY: CDS
<222> LOCATION: (1)..(48)

<400> SEQUENCE: 5 tac tac aac tat tat agc aac tac tat ggt cgc agt tac agc agt gac      48
Tyr Tyr Asn Tyr Tyr Ser Asn Tyr Tyr Gly Arg Ser Tyr Ser Ser Asp
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Tyr Tyr Asn Tyr Tyr Ser Asn Tyr Tyr Gly Arg Ser Tyr Ser Ser Asp
1               5                   10                  15

<210> SEQ ID NO 7
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: TOP2
<220> FEATURE:
<221> NAME/KEY: CDS
<222> LOCATION: (1)..(48)

<400> SEQUENCE: 7 tac tat gat tac tat tac agc tac aat gat ggc gac tat cgc ggt tgc      48
Tyr Tyr Asp Tyr Tyr Tyr Ser Tyr Asn Asp Gly Asp Tyr Arg Gly Cys
1               5                   10                  15
```

```
<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Tyr Tyr Asp Tyr Tyr Tyr Ser Tyr Asn Asp Gly Asp Tyr Arg Gly Cys
1               5                   10                  15

<210> SEQ ID NO 9
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: TOP3
<220> FEATURE:
<221> NAME/KEY: CDS
<222> LOCATION: (1)..(48)

<400> SEQUENCE: 9 tac tac aac tac tat tat ggt tat cgt tac gac ggt ggt cgt ggt tgc      48
Tyr Tyr Asn Tyr Tyr Tyr Gly Tyr Arg Tyr Asp Gly Gly Arg Gly Cys
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Tyr Tyr Asn Tyr Tyr Tyr Gly Tyr Arg Tyr Asp Gly Gly Arg Gly Cys
1               5                   10                  15

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aaacagctat gaccatgatt a                                              21

<210> SEQ ID NO 12
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttaatacgac tcactataga aaagtcgaca ataattttgt ttaactt                  47

<210> SEQ ID NO 13
<211> LENGTH: 4422
<212> TYPE: DNA
<213> ORGANISM: Artificial Sequence
```

<220> FEATURE:
<223> OTHER INFORMATION: Description of Artificial Sequence: Synthetic plasmid polynucleotide

<400> SEQUENCE: 13

```
cttccgcttc ctcgctcact gactcgctgc gctcggtcgt tcggctgcgg cgagcggtat    60
cagctcactc aaaggcggta atacggttat ccacagaatc aggggataac gcaggaaaga   120
acatgtgagc aaaaggccag caaaaggcca ggaaccgtaa aaaggccgcg ttgctggcgt   180
ttttccatag gctccgcccc cctgacgagc atcacaaaaa tcgacgctca agtcagaggt   240
ggcgaaaccc gacaggacta taaagatacc aggcgtttcc ccctggaagc tccctcgtgc   300
gctctcctgt tccgaccctg ccgcttaccg gatacctgtc cgcctttctc ccttcgggaa   360
gcgtggcgct ttctcatagc tcacgctgta ggtatctcag ttcggtgtag gtcgttcgct   420
ccaagctggg ctgtgtgcac gaaccccccg ttcagcccga ccgctgcgcc ttatccggta   480
actatcgtct tgagtccaac ccggtaagac acgacttatc gccactggca gcagccactg   540
gtaacaggat tagcagagcg aggtatgtag gcggtgctac agagttcttg aagtggtggc   600
ctaactacgg ctacactaga agaacagtat ttggtatctg cgctctgctg aagccagtta   660
ccttcggaaa aagagttggt agctcttgat ccggcaaaca accaccgct ggtagcggtg    720
gtttttttgt ttgcaagcag cagattacgc gcagaaaaaa aggatctcaa gaagatcctt   780
tgatcttttc tacggggtct gacgctcagt ggaacgaaaa ctcacgttaa gggattttgg   840
tcatgagatt atcaaaaagg atcttcacct agatcctttt aaattaaaaa tgaagtttta   900
aatcaatcta aagtatatat gagtaaactt ggtctgacag ttaccaatgc ttaatcagtg   960
aggcacctat ctcagcgatc tgtctatttc gttcatccat agttgcctga ctccccgtcg  1020
tgtagataac tacgatacgg gagggcttac catctggccc cagtgctgca atgataccgc  1080
gagacccacg ctcaccggct ccagatttat cagcaataaa ccagccagcc ggaagggccg  1140
agcgcagaag tggtcctgca actttatccg cctccatcca gtctattaat tgttgccggg  1200
aagctagagt aagtagttcg ccagttaata gtttgcgcaa cgttgttgcc attgctacag  1260
gcatcgtggt gtcacgctcg tcgtttggta tggcttcatt cagctccggt tcccaacgat  1320
caaggcgagt tacatgatcc cccatgttgt gcaaaaaagc ggttagctcc ttcggtcctc  1380
cgatcgttgt cagaagtaag ttggccgcag tgttatcact catggttatg gcagcactgc  1440
ataattctct tactgtcatg ccatccgtaa gatgcttttc tgtgactggt gagtactcaa  1500
ccaagtcatt ctgagaatag tgtatgcggc gaccgagttg ctcttgcccg gcgtcaatac  1560
gggataatac cgcgccacat agcagaactt taaaagtgct catcattgga aaacgttctt  1620
cggggcgaaa actctcaagg atcttaccgc tgttgagatc cagttcgatg taacccactc  1680
gtgcacccaa ctgatcttca gcatctttta ctttcaccag cgtttctggg tgagcaaaaa  1740
caggaaggca aaatgccgca aaaaagggaa taagggcgac acggaaatgt tgaatactca  1800
tactcttcct ttttcaattc agaagaactc gtcaagaagg cgatagaagg cgatgcgctg  1860
cgaatcggga gcggcgatac cgtaaagcac gaggaagcgg tcagcccatt cgccgccaag  1920
ctcttcagca atatcacggg tagccaacgc tatgtcctga tagcggtccg ccacacccag  1980
ccggccacag tcgatgaatc cagaaaagcg gccattttcc accatgatat tcggcaagca  2040
ggcatcgcca tgggtcacga cgagatcctc gccgtcgggc atgcgcgcct tgagcctggc  2100
gaacagttcg gctggcgcga gcccctgatg ctcttcgtcc agatcatcct gatcgacaag  2160
accggcttcc atccgagtac gtgctcgctc gatgcgatgt ttcgcttggt ggtcgaatgg  2220
```

-continued

```
gcaggtagcc ggatcaagcg tatgcagccg ccgcattgca tcagccatga tggatacttt    2280
ctcggcagga gcaaggtggg atgacaggag atcctgcccc ggcacttcgc ccaatagcag    2340
ccagtcccct cccgcttcag tgacaacgtc gagcacagct gcgcaaggaa cgcccgtcgt    2400
ggccagccac gatagccgcg ctgcctcgtc ctgcagttca ttcagggcac cggacaggtc    2460
ggtcttgaca aaaagaaccg ggcgcccctg cgctgacagc cggaacacgg cggcatcaga    2520
gcagccgatt gtctgttgtg cccagtcata gccgaatagc ctctccaccc aagcggccgg    2580
agaacctgcg tgcaatccat cttgttcaat catgcgaaac gatcctcatc ctgtctcttg    2640
atcagatctt gatccctgc gccatcagat ccttggcggc aagaaagcca tccagtttac    2700
tttgcagggc ttcccaacct taccagaggg cgccccagct ggcaattccg gttcgcttgc    2760
tgtccataaa accgcccagt ctagctatcg ccatgtaagc ccactgcaag ctacctgctt    2820
tctctttgcg cttgcgtttt cccttgtcca gatagcccag tagctgacat tcatccgggg    2880
tcagcaccgt ttctgcggac tggctttcta cgtgttccgc ttcctttagc agcccttgcg    2940
ccctgaattt tgttaaaatt cgcgttaaat ttttgttaaa tcagctcatt ttttaaccaa    3000
taggccgaaa tcggcaaaat cccttataaa tcaaaagaat agaccgagat agggttgagt    3060
gttgttccag tttggaacaa gagtccacta ttaaagaacg tggactccaa cgtcaaaggg    3120
cgaaaaaccg tctatcaggg cgatggccca ctacgtgaac catcaccccta atcaagtttt    3180 ttggggtcga ggtgccgtaa agcactaaat cggaacccta agggagcccc cgatttaga    3240 gcttgacggg gaaagccggc gaacgtggcg agaaaggaag gaagaaagc gaaggagcg    3300 ggcgctaggg cgctggcaag tgtagcggtc acgctgcgcg taaccaccac acccgccgcg    3360
cttaatgcgc cgctacaggg cgcgtccatt cgccattcag gctgcgcaac tgttgggaag    3420
ggcgatcggt gcgggcctct tcgctattac gccagctggc gaaaggggga tgtgctgcaa    3480
ggcgattaag ttgggtaacg ccaggggttttt cccagtcacg acgttgtaaa acgacggcca    3540
gtgaattgta atacgactca ctatagggcg aattgggccc tctagatgca tgctcgagcg    3600
gccgcgtcga caataatttt gtttaacttt aagaaggaga tatacatatg gccatgcagg    3660
ccagctaggc cagttcgaag gtaatagtga ctctgaatgt cccctgtccc acgatgggta    3720
ctgcctccat gatggtgtgt gcatgtatat tgaagcattg gacaagtatg catgcaactg    3780
tgttgttggc tacatcgggg agcgatgtca gtaccgagac ctgaagtggt gggaactgcg    3840
cttcgaatct gatgttgaag agaatcgcac tgaagctcca gaaggtaccg agtctgaaat    3900
ggaaacacca tcggccatca acggtaatcc gtcgtggcac ctggccgata gcccagctgt    3960
gaatggtgct actggaggtt cgagctctga cgttgaagag aaccgcaccg aggcaccaga    4020
aggaaccgaa tccgaaatgg agacaccgtc tgctatcaac ggcaatccat cgtggcacct    4080
cgctgactct ccagccgtca atggagctac cgggatccag ttttctactc ctgtttggat    4140
ttctcaagct caaggtattc gtgctggtcc tcaacgtctc actcagcttg gcgtaatcat    4200
ggtcatagct gtttcctgtg tgaaattgtt atccgctcac aattccacac aacatacgag    4260
ccggaagcat aaagtgtaaa gcctggggtg cctaatgagt gagctaactc acattaattg    4320
cgttgcgctc actgcccgct ttccagtcgg gaaacctgtc gtgccagctg cattaatgaa    4380
tcggccaacg cgcggggaga ggcggtttgc gtattgggcg ct                       4422
```

<210> SEQ ID NO 14
<211> LENGTH: 80
<212> TYPE: PRT
<213> ORGANISM: Artificial Sequence

```
<220> FEATURE:
<223> OTHER INFORMATION: Description of Artificial Sequence: Synthetic
      polypeptide
<220> FEATURE:
<223> OTHER INFORMATION: sTOP1-EGF

<400> SEQUENCE: 14

Met Gln Ala Tyr Tyr Asn Tyr Tyr Ser Asn Tyr Tyr Gly Arg Ser Tyr
1               5                   10                  15

Ser Ser Asp Gly Gln Leu Gly Gln Phe Glu Gly Asn Ser Asp Ser Glu
            20                  25                  30

Cys Pro Leu Ser His Asp Gly Tyr Cys Leu His Asp Gly Val Cys Met
        35                  40                  45

Tyr Ile Glu Ala Leu Asp Lys Tyr Ala Cys Asn Cys Val Val Gly Tyr
    50                  55                  60

Ile Gly Glu Arg Cys Gln Tyr Arg Asp Leu Lys Trp Trp Glu Leu Arg
65                  70                  75                  80

<210> SEQ ID NO 15
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: TOP4
<220> FEATURE:
<221> NAME/KEY: CDS
<222> LOCATION: (1)..(48)

<400> SEQUENCE: 15 tat tat ggt cgt tac agc gac tat tat gac aat ggt tac ggt cgt cgt    48
Tyr Tyr Gly Arg Tyr Ser Asp Tyr Tyr Asp Asn Gly Tyr Gly Arg Arg
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Tyr Tyr Gly Arg Tyr Ser Asp Tyr Tyr Asp Asn Gly Tyr Gly Arg Arg
1               5                   10                  15

<210> SEQ ID NO 17
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: TOP5
<220> FEATURE:
<221> NAME/KEY: CDS
<222> LOCATION: (1)..(48)

<400> SEQUENCE: 17 tat aac cgt tat gat ggc cgc tac tac cgt gat cac ggt cgt aat tac    48
Tyr Asn Arg Tyr Asp Gly Arg Tyr Tyr Arg Asp His Gly Arg Asn Tyr
1               5                   10                  15
```

```
<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Tyr Asn Arg Tyr Asp Gly Arg Tyr Tyr Arg Asp His Gly Arg Asn Tyr
1               5                   10                  15

<210> SEQ ID NO 19
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: TOP6
<220> FEATURE:
<221> NAME/KEY: CDS
<222> LOCATION: (1)..(39)

<400> SEQUENCE: 19 tac aat gat tac tac tac tac tgc tat cgc gac tat gac                    39
Tyr Asn Asp Tyr Tyr Tyr Tyr Cys Tyr Arg Asp Tyr Asp
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Tyr Asn Asp Tyr Tyr Tyr Tyr Cys Tyr Arg Asp Tyr Asp
1               5                   10

<210> SEQ ID NO 21
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Tyr, Asn or a derivative thereof
<220> FEATURE:
<221> NAME/KEY: MOD_RES
<222> LOCATION: (3)..(3)
<223> OTHER INFORMATION: Asn, Asp, Gly, Arg or a derivative thereof
<220> FEATURE:
<221> NAME/KEY: MOD_RES
<222> LOCATION: (6)..(6)
<223> OTHER INFORMATION: Ser, Tyr, Gly or a derivative thereof
<220> FEATURE:
<221> NAME/KEY: MOD_RES
<222> LOCATION: (7)..(7)
<223> OTHER INFORMATION: Asn, Ser, Gly, Arg, Asp or a derivative thereof
<220> FEATURE:
<221> NAME/KEY: MOD_RES
<222> LOCATION: (9)..(9)
<223> OTHER INFORMATION: Tyr, Asn, Arg or a derivative thereof
<220> FEATURE:
<221> NAME/KEY: MOD_RES
<222> LOCATION: (10)..(10)
<223> OTHER INFORMATION: Gly, Asp, Tyr, Arg or a derivative thereof
```

```
<220> FEATURE:
<221> NAME/KEY: MOD_RES
<222> LOCATION: (11)..(11)
<223> OTHER INFORMATION: Arg, Gly, Asp, Asn or a derivative thereof
<220> FEATURE:
<221> NAME/KEY: MOD_RES
<222> LOCATION: (12)..(12)
<223> OTHER INFORMATION: Ser, Asp, Gly, His or a derivative thereof
<220> FEATURE:
<221> NAME/KEY: MOD_RES
<222> LOCATION: (13)..(13)
<223> OTHER INFORMATION: Tyr, Gly or a derivative thereof
<220> FEATURE:
<221> NAME/KEY: MOD_RES
<222> LOCATION: (14)..(14)
<223> OTHER INFORMATION: Ser, Arg, Gly or a derivative thereof
<220> FEATURE:
<221> NAME/KEY: MOD_RES
<222> LOCATION: (15)..(15)
<223> OTHER INFORMATION: Ser, Gly, Arg, Asn or a derivative thereof
<220> FEATURE:
<221> NAME/KEY: MOD_RES
<222> LOCATION: (16)..(16)
<223> OTHER INFORMATION: Asp, Cys, Arg, Tyr or a derivative thereof
<220> FEATURE:
<223> OTHER INFORMATION: see specification as filed for detailed
      description of substitutions and preferred embodiments

<400> SEQUENCE: 21

Tyr Xaa Xaa Tyr Tyr Xaa Xaa Tyr Xaa Xaa Xaa Xaa Xaa Xaa Xaa
1               5                   10                  15

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Lys Leu Pro Asp Ala Pro Gly Met His Thr Trp
1               5                   10

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 23

His His His His His His
1               5
```

METHOD OF SELECTING POLYPEPTIDE SEQUENCE, AND METAL OXIDE OR SILICON-CONTAINING COMPOUND BINDING PEPTIDE AND USE THEREOF

This application is a continuation-in-part under 35 U.S.C. §120 of PCT Patent Application No. PCT/JP2011/055815, filed Mar. 11, 2011, which claims priority under 35 U.S.C. §119 to Japanese Patent Application No. 2010-054927, filed on Mar. 11, 2010, which are incorporated in their entireties by reference.

SEQUENCE LISTING

The instant application contains a Sequence Listing which has been submitted in ASCII format via EFS-Web and is hereby incorporated by reference in its entirety. Said ASCII copy, created on Oct. 22, 2012, is named P42622.txt and is 21,574 bytes in size.

BACKGROUND OF THE INVENTION

1. Field of the Invention

The present invention relates to a method of selecting a polypeptide sequence which imparts a target substance binding-ability to a protein of interest and a nucleic acid construct using therefor. The present invention also relates to a peptide that binds specifically to a metal oxide or a silicon-containing compound, and a method of producing a fusion protein using the peptide, a method of purifying the fusion protein, a method of immobilizing the protein, as well as a surface treatment agent for biomaterials and the like.

2. Brief Description of the Related Art

The term "peptide aptamer" is a general term for an artificial peptide that binds specifically to a specific target molecule. At present, not only does a peptide aptamer exhibiting a binding function similar to an "antibody" draw much attention as a probe for molecular detection in the field of chemistry, biology, and medical science; but also is anticipated in the field of medicine as a molecular target drug for the next generation in place of an antibody pharmaceutical.

In order to obtain peptide aptamers that bind specifically to a specific target molecule, screening for the peptide aptamers is carried out by repeating a cycle composed of: expressing random polypeptides from DNAs encoding the random polypeptides; bringing them into contact with target molecule; selecting one that binds specifically to the target molecule; and amplifying a DNA which encodes it.

For such a screening, a technique such as phage display (G. P. Smith et al. (1985) Science, vol. 228, p. 1315-1317), ribosome display (JP3127158B, JP2001-521395A, JP2002-500514A, WO 01/75097, and J Hanes and A Pluckthun (1997) Proc Natl Acad Sci USA, vol. 94, p. 4937-4942), or mRNA display (L. C. Mattheakis et al. (1994) Proc Natl Acad Sci USA, vol. 91, p. 9022-9026, R. W. Roberts et al. (1997) Proc Natl Acad Sci USA, vol. 94, p. 12297-12302 and N. Nemoto et al. (1997) FEBS Lett., vol. 414, p. 405-408) has been employed. A polypeptide selected by a screening method using such a display technique comes with genetic information encoding its amino acid sequence, and thus the selected polypeptide can be promptly amplified in large amounts by genetic engineering process based on the genetic information encoding it. In addition, by analyzing the genetic information, the amino acid sequence can be readily identified.

Development of the display technique described above has made it possible to screen a target substance binding peptide efficiently. However, when a target substance binding-ability is imparted to a protein of interest by fusing the obtained target substance binding peptide to the protein of interest, it has often happened, albeit depending on the type of protein, that the fusion protein does not show the target substance binding-ability due to problems concerning spatial structures and the like.

Meanwhile, a metal oxide and a silicon-containing compound have been recently drawn much attention as medical materials. In view of this, it is considered that obtaining a peptide that binds specifically to a metal oxide or a silicon-containing compound allows various modification of the surface of medical materials containing a metal oxide or a silicon-containing compound, which is useful for providing the medical materials with multiple functions.

The present inventors have reported a peptide having a histidine-rich amino acid sequence as the peptide that binds specifically to a metal oxide or a silicon-containing compound (JP 2009-136280A). In addition, a titanium dioxide binding peptide TBP-1 has been reported in K Shiba et al., Langmuir (2005), vol. 21, p 3090, and K Shiba et al., Nano Lett. (2006), vol. 6, p 515.

SUMMARY OF THE INVENTION

An object of the present invention is to provide a method of efficiently selecting a polypeptide sequence which imparts a target substance binding-ability to a protein of interest, and to provide a peptide that binds specifically to a metal oxide and/or a silicon-containing compound.

The present inventors intensively studied in order to solve the object above. As a result, they found that a polypeptide sequence which imparted a target substance binding-ability to a protein of interest could be efficiently selected by screening using a nucleic acid construct as a library, which nucleic acid construct comprising a first nucleotide sequence encoding a random polypeptide and a second nucleotide sequence which is linked to the first nucleotide sequence in flame and encodes the protein of interest or part thereof. Furthermore, using the method above, they found peptide sequences that bind specifically to a metal oxide and/or a silicon-containing compound and found that, by using it, the surface of a biomaterial being composed of the metal oxide or the silicon-containing compound could be provided with higher functions, thereby completing the present invention.

That is, the present invention provides the followings.

[1] A method of selecting a polypeptide sequence which imparts a target substance binding-ability to a protein of interest, said method comprises repeating the following steps (1) to (3);

(1) expressing a library of fusion proteins, each of which is composed of a random polypeptide and a protein of interest or part thereof, from a nucleic acid construct comprising a first nucleotide sequence encoding the random polypeptide and a second nucleotide sequence which is linked to the first nucleotide sequence in flame and encodes the protein of interest or part thereof, (2) contacting the library with a target substance, (3) selecting a fusion protein which comprises a polypeptide sequence that binds to the target substance, and amplifying a nucleic acid construct which encodes the selected fusion protein.

[2] The method according to [1], wherein the protein of interest is a cell growth factor.

[3] The method according to [2], wherein the cell growth factor is an epidermal growth factor.

[4] The method according to any one of [1] to [3], wherein the nucleic acid construct comprises a promoter sequence, a Shine-Dalgarno sequence, and a start codon in the 5' side of the first nucleotide sequence.

[5] The method according to any one of [1] to [4], wherein the nucleic acid construct comprises a nucleotide sequence encoding a spacer sequence and/or a SecM sequence in the 3' side of the second nucleotide sequence.

[6] The method according to [5], wherein the spacer sequence is the amino acid sequence of amino acid numbers 85 to 173 in SEQ ID NO: 2 or the same amino acid sequence but including substitutions, deletions, insertions or additions of one or several amino acids.

[7] The method according to any one of [1] to [6], wherein the library of fusion proteins is expressed by a ribosome display method.

[8] The method according to any one of [1] to [7], wherein the target substance is a metal oxide or a silicon-containing compound.

[9] A nucleic acid construct comprising, in the order mentioned from the 5' side, a first nucleotide sequence encoding a promoter sequence, a Shine-Dalgarno sequence, a start codon, and a random polypeptide; and a second nucleotide sequence which is linked to the first nucleotide sequence in flame and encodes a protein of interest or part thereof.

[10] The nucleic acid construct according to [9], further comprising a nucleotide sequence encoding a spacer sequence and/or a SecM sequence in the 3' side of the second nucleotide sequence.

[11] The nucleic acid construct according to [10], wherein the spacer sequence is an amino acid sequence of amino acid numbers 85 to 173 in SEQ ID NO: 2 or the same amino acid sequence but including substitutions, deletions, insertions or additions of one or several amino acids.

[12] A peptide comprising the following amino acid sequence:
Tyr-$Xaa^0$-$Xaa^1$-Tyr-Tyr-$Xaa^2$-$Xaa^3$-Tyr-$Xaa^4$-$Xaa^5$-$Xaa^6$-$Xaa^7$-$Xaa^8$-$Xaa^9$-$Xaa^{10}$-$Xaa^{11}$ (SEQ ID NO: 4; wherein $Xaa^0$, $Xaa^1$, $Xaa^2$, $Xaa^3$, $Xaa^4$, $Xaa^5$, $Xaa^6$, $Xaa^7$, $Xaa^8$, $Xaa^9$, $Xaa^{10}$ and $Xaa^{11}$ represent any amino acid).

[13] The peptide according to [12], wherein $Xaa^0$ is Tyr, Asn or a derivative thereof; $Xaa^1$ is Asn, Asp, Gly, Arg or a derivative thereof; $Xaa^2$ is Ser or a derivative thereof, Tyr, Gly; $Xaa^3$ is Asn, Ser, Gly, Arg, Asp or a derivative thereof; $Xaa^4$ is Tyr, Asn, Arg or a derivative thereof; $Xaa^5$ is Gly, Asp, Tyr, Arg or a derivative thereof; $Xaa^6$ is Arg, Gly, Asp, Asn or a derivative thereof; $Xaa^7$ is Ser, Asp, Gly, His or a derivative thereof; $Xaa^8$ is Tyr, Gly or a derivative thereof; $Xaa^9$ is Ser, Arg, Gly or a derivative thereof; $Xaa^{10}$ is Ser, Gly, Arg, Asn or a derivative thereof; $Xaa^{11}$ is Asp, Cys, Arg, Tyr or a derivative thereof (SEQ ID NO: 21).

[14] The peptide according to [12] comprising an amino acid sequence selected from the group consisting of SEQ ID NOs: 6, 8, 10, 16 and 18.

[15] A peptide comprising an amino acid sequence of SEQ ID NO: 20.

[16] A fusion protein comprising the peptide according to any one of [12] to [15] and a protein or part thereof linked to the peptide.

[17] The fusion protein according to [16], wherein the protein is a cell growth factor.

[18] The fusion protein according to [17], wherein the cell growth factor is an epidermal growth factor.

[19] A polynucleotide encoding the peptide according to any one of [12] to [15] or the fusion protein according to any one of [16] to [18].

[20] A vector comprising the polynucleotide according to [19].

[21] A method of producing a protein comprising introducing a vector comprising a polynucleotide encoding the fusion protein according to any one of [16] to [18] into a host cell or an in vitro translation system to express the fusion protein; and collecting the fusion protein.

[22] The method according to [21], wherein the fusion protein is collected using a metal oxide or a silicon-containing compound.

[23] A method of purifying a protein comprising contacting a sample containing the fusion protein according to any one of [16] to [18] with a metal oxide or a silicon-containing compound to bind the fusion protein in the sample with the metal oxide or the silicon-containing compound; and collecting the fusion protein that binds to the metal oxide or the silicon-containing compound.

[24] A kit for expressing and purifying a protein, comprising a fine particle of a metal oxide or a silicon-containing compound and the vector according to [20].

[25] A method of immobilizing a protein comprising immobilizing the fusion protein according to any one of [16] to [18] on a substrate, wherein at least the surface of the substrate is composed of a metal oxide or a silicon-containing compound and the protein is immobilized via the metal oxide or the silicon-containing compound.

[26] A method of immobilizing a bioactive substance comprising immobilizing a bioactive substance via a metal oxide or a silicon-containing compound by contacting a bioactive substance bound to the peptide according to any one of [12] to [15] on a substrate at least the surface of which is composed of the metal oxide or the silicon-containing compound.

[27] An antibody against the peptide according to any one of [12] to [15].

[28] A surface treatment agent for a biomaterial containing a metal oxide or a silicon-containing compound, the surface treatment agent comprising a bioactive substance bound to the fusion protein according to any one of [16] to [18] or the peptide according to any one of [12] to [15].

[29] A biomaterial wherein a bioactive substance bound to the fusion protein according to any one of [16] to [18] or the peptide according to any one of [12] to [15] has been immobilized on a substrate at least the surface of which is composed of a metal oxide or a silicon-containing compound.

[30] A pharmaceutical comprising a biomaterial wherein a bioactive substance bound to the fusion protein according to [17] or [18] or the peptide according to any one of [12] to [15] has been immobilized on a substrate at least the surface of which is composed of a metal oxide or a silicon-containing compound, which pharmaceutical is used in regenerative medicine by inducing a cell onto the biomaterial.

According to a method of the present invention, a polypeptide sequence which imparts a target substance binding-ability to a protein of interest can be efficiently selected.

In addition, by using the peptide sequence of the present invention, a protein can be imparted a binding ability to a metal oxide or a silicon-containing compound. This enables the protein to be purified and immobilized using the metal oxide or the silicon-containing compound. In addition, by modifying surfaces of a biomaterial composed of the metal oxide or the silicon-containing compound using a fusion protein which comprises the peptide sequence of the present invention, the protein, a biologically active substance, or the like can be induced to the surface of the biomaterial, which can provide the biomaterial with higher functions.

BRIEF DESCRIPTION OF THE DRAWINGS

FIG. 1 shows a schematic diagram of a method of screening a peptide which imparts a titanium dioxide-binding ability to epidermal growth factor (EGF) using the ribosome display which is one mode of the present invention.

FIG. 2 shows a schematic diagram (1) and base sequence (2) of a DNA construct used in the screening. In (2), the boxed portion indicates a sequence encoding the random peptide; the double-underlined portion indicates a sequence encoding EGF; the oblique type portion indicates a sequence encoding a spacer; and the broken line indicates a sequence encoding SecM. EGF corresponds to amino acid numbers 30 to 82 in SEQ ID NO: 2.

FIG. 3 shows the structure of various peptide fusion EGFs (P-EGFs) and their expression in a cell free protein translation system (a schematic diagram and photograph of electrophoresis). FIG. 3 discloses "H6" as SEQ ID NO: 23.

FIG. 4 shows evaluation of the binding ability of various P-EGFs to titanium dioxide (a schematic diagram and photograph of binding analysis). The evaluation was carried out: 1) for binding to titanium dioxide particles; and 2) for binding to the surface of the titanium dioxide plate. FIG. 4 discloses "H6" as SEQ ID NO: 23.

FIG. 5 shows evaluation of the binding ability of various P-EGFs to the silicon dioxide plate (a schematic diagram and photograph of binding analysis). FIG. 5 discloses "H6" as SEQ ID NO: 23.

FIG. 6 shows evaluation of cell proliferation on the titanium dioxide plate with or without TOP1-EGF surface modification (a schematic diagram and photograph). 1: epidermal keratinocytes and 2: NIH-3T3 cells.

FIG. 7 shows evaluation of the binding ability of chemically synthesized TOP1-EGF (sTOP1-EGF) to the titanium dioxide plate; and evaluation of NRK-49F cell proliferation on the titanium dioxide plate with or without sTOP1-EGF surface modification (a schematic diagram and photograph).

DESCRIPTION OF THE EMBODIMENTS

<A Method of Selecting a Polypeptide Sequence which Imparts a Target Substance Binding-Ability to a Protein of Interest>

A method of selecting a polypeptide sequence which imparts a target substance binding ability to a protein of interest is characterized in that the following steps (1) to (3) are repeated;

(1) the step of expressing a library of fusion proteins, each of which is composed of a random polypeptide and a protein of interest or part thereof, from a nucleic acid construct comprising a first nucleotide sequence encoding the random polypeptide and a second nucleotide sequence which is linked to the first nucleotide sequence in flame and encodes the protein of interest or part thereof, (2) the step of contacting the target substance with the above-mentioned library, and (3) the step of selecting a fusion protein which comprises a polypeptide sequence that binds to the target substance and amplifying a nucleic acid construct which encodes the selected fusion protein.

Here, the protein of interest may be in full length or part thereof such as a DNA binding region, a ligand binding region, an active region, or the like.

The type of the protein of interest is not especially restricted but examples thereof include an enzyme, an antibody, a signal transduction factor, a channel, a cell growth factor, a transcription factor, an adhesion factor, a receptor, and the like. Also, it may be a protein with unknown functions.

As the protein of interest, a polypeptide having a natural sequence derived from any organisms, for example, mammals including human, plants, viruses, yeast, or bacteria, can be used. Alternatively, a part of the natural polypeptide or a mutant polypeptide whose amino acid sequence is modified can be used as the protein of interest. Furthermore, a polypeptide containing an artificially designed amino acid sequence may be used as the protein of interest The target substance can be any substance as long as a protein or peptide can bind to it, and examples thereof include a low molecular weight compound, a peptide, a metal (including metal salt and metal oxide), a silicon-containing compound, and the like.

Described below is a nucleic acid construct comprising a first nucleotide sequence encoding a random polypeptide and a second nucleotide sequence which is linked to the first nucleotide sequence in flame and encodes a protein of interest or part thereof.

The random polypeptide refers to one having a sequence in which any amino acids are randomly placed. The random polypeptide has a random amino acid sequence containing approximately not less than 3 residues, usually 5 to 100 residues, preferably 5 to 50 residues or 5 to 20 residues in length. The amino acids may be naturally occurring or non-naturally occurring ones, or a mixture thereof. More simply, the random polypeptide is composed of one or more amino acids selected from 20 naturally occurring amino acids.

To have a completely random sequence (the number of the amino acid residues is n) in the polypeptide, 3n of A, T, G, and C may be randomly placed. Yet, in order to for a clone to be efficiency translated, a base at the 3m th position (m=1, 2, 3, ..., n) may be T or C such that appearance of a stop codon can be avoided. Alternatively, codons may be adjusted such that the random sequence is composed of one or more specific kind of amino acids alone.

For instance, as described in the examples later, by using repeats of a NRY codon, a peptide sequence in which eight kinds of amino acids (Ser, Asn, Gly, Asp, Arg, His, Cys or/and Tyr) randomly appear can be expressed.

N=A, G, C, T
R=A, G
Y=C, T

When the random polypeptide contains non-naturally occurring amino acids, the codon may be modified in accordance with a known means.

A second nucleotide sequence encoding a protein of interest or part thereof is linked in flame to the first nucleotide sequence which encodes the above random polypeptide.

The term "is linked in flame to" herein means the random polypeptide and the protein of interest or part thereof are linked so as to be translated as a fusion protein. The random polypeptide and the protein of interest or part thereof may be linked directly or through an amino acid sequence with 1 to several amino acids (for example, 1 to 10 amino acids).

The first nucleotide sequence encoding the random polypeptide can be artificially synthesized and linked to the nucleotide sequence encoding the protein of interest or part thereof using a restriction enzyme recognition sequence or using PCR by a genetic engineering process. Yet, the whole of the first nucleotide sequence which encodes the random polypeptide and the second nucleotide sequence which encodes the protein of interest or part thereof may be artificially synthesized.

The above nucleic acid construct preferably contains, in the order mentioned from the 5' side, a promoter sequence, the Shine-Dalgarno (SD) sequence, and a start codon in the 5' side of the first nucleotide sequence.

A promoter can be selected according to an expression system to be used. For instance, in the case of using *Escherichia coli* cells or a cell free translation system of *Escherichia coli* origin, examples of the promoter include a T7 promoter, a T3 promoter, an SP6 promoter and the like, all of which promoters function in *Escherichia coli*.

The above nucleic acid construct preferably contains a nucleotide sequence encoding at least either one of a spacer sequence or the SecM sequence in the 3' side of the second nucleotide sequence.

In order to increase the degrees of freedom of the fusion protein composed of the random peptide and the protein of interest or part thereof, it is preferred that the spacer sequence have a sequence with 10 to 200 amino acids. The amino acid sequence of the spacer sequence is not particularly restricted as long as it does not adversely affected a binding reaction between the fusion protein and a target substance, but it is particularly preferred that the sequence is an amino acid sequence of amino acid numbers 85 to 173 in SEQ ID NO: 2 (FIG. 2).

The sequence is a novel sequence obtained by uniquely extracting a sequence whose "degrees of freedom is thought to be too high" to be identified by X-ray crystallography of Bcl-xL, and appropriately introducing Gly to it for achieving higher flexibility. The expression level of EGF fused with this sequence is tremendously higher as compared with that of EGF fused with other protein spacer, which enables efficient screening.

This sequence may be partially modified as long as the binding reaction between the fusion protein and the target substance is not inhibited. That is, the spacer sequence may be the same sequence except that 1 or several amino acids (preferably 2 to 10 amino acids, more preferably 2 to 5 amino acids) are substituted, deleted, inserted, or added in amino acid numbers 85 to 173 in SEQ ID NO: 2.

It can be expected that use of the above spacer sequence to produce the fusion protein improves translation efficiency of a protein which is not easily expressed in the cell free translation system. In addition, application of this sequence as a linker for connecting a functional protein with a protein can potentially help development of a protein probe and/or protein sensor used in intracellular and extracellular imaging and in vivo imaging.

The SecM sequence is also referred to as the SecM stall sequence and a sequence which is reported to cause translation arrest inside the ribosome (FXXXXWIXXXXGIRAGP: SEQ ID NO: 3). In SEQ ID NO: 2, the SecM sequence corresponds to the sequence of amino acid numbers 176 to 192 (FIG. 2). Introduction of the arrest sequence of SecM enables a complex composed of mRNA, ribosome, fusion protein to be efficiently maintained and thus the sequence is particularly beneficial for a ribosome display.

SEQ ID NO: 1 shows a nucleic acid construct comprising, in the order mentioned from the 5' side, a nucleotide sequence encoding a promoter sequences, the SD sequence, a start codon, and a random polypeptide and a nucleotide sequence which is linked in flame thereto and encodes a protein of interest (EGF), a nucleotide sequence encoding a spacer sequence and the SecM sequence (FIG. 2). And SEQ ID NO: 2 shows the amino acid sequence of a fusion protein translated from SEQ ID NO: 1 (including the spacer and SecM sequences). The nucleic acid construct of the present invention and the fusion protein encoded thereby are not limited thereto.

The above nucleic acid construct may be incorporated into a plasmid vector, a phage vector, a viral vector or the like. The type of vector can be appropriately selected according to a translation system or a screening system.

The above nucleic acid construct and the vector comprising it can be prepared by known genetic techniques described in Molecular Cloning (Cold Spring Harbor Laboratory Press, Cold Spring Harbor (USA), 2001) or the like.

Next, each step will be described below.

First, a library of fusion proteins, each of which is composed of a random polypeptide and a protein of interest or part thereof is expressed from the above nucleic acid construct.

For the expression, host cells such as *Escherichia coli*, yeast, or mammalian cells, viruses, phages, or a cell free translation system can be used. For efficient screening, it is preferred that a display system be used.

The display system refers to a system in which a polypeptide expressed from a library comes with nucleic acids (genetic information) encoding its amino acid sequence. In other words, it refers to a system in which the genetic information is displayed as a polypeptide encoded thereby. As for the type of display, a phage display, an in vitro display and the like are known. In addition, as for the in vitro display, a ribosome display, an mRNA display, and the like are known.

In the phage display, a gene encoding a constituent protein of filamentous phage is, in general, linked to a gene encoding a polypeptide to be displayed. As a result, as a fusion protein with a structure protein of the phage, the polypeptide is displayed on the surface of the phage (G. P. Smith et al. (1985) Science, vol. 228, p. 1315-1317).

In the phage display, in order to obtain the genetic information of polypeptide that binds to a target polypeptide/protein, phages which do not bind to the target polypeptide/protein are removed by washing and then the phage displaying the polypeptide that binds to the target polypeptide/protein is eluted, followed by the steps of infecting the phage into *Escherichia coli* and of proliferating it. In cases where panning is repeated, the steps of infection into *Escherichia coli* and proliferation of the phage are repeated as well.

As for the phage display system, for example, a kit such as T7 Select (R) Phage Display System (manufactured by Novagen) is commercially available. Use of such a kit enables genetic information of an arbitrary cDNA library to be displayed on phage as a polypeptide. In addition, as for a library for screening, a commercially available library such as Premade T7 Select (R) cDNA Libraries (manufactured by Novagen) or the like can be used.

In the ribosome display, by using a cell free translation system obtained from cells of *Escherichia coli* or the like, a polypeptide is synthesized based on given genetic information. In living cells, due to on-going mechanism to dissociate the synthesized polypeptide from the ribosome, a link between these two is usually not maintained. However, in the ribosome display, the dissociation between the two is inhibited and a displayed polypeptide is thus maintained while keeping the genetic information (mRNA) encoding it. Thus, a complex of three elements: mRNA, ribosome, and polypeptide, is formed. By collecting mRNA of polypeptide that binds to the target, its genetic information is also collected.

In the mRNA display, by chemically binding of the polypeptide with mRNA, a link between these two is maintained. For the binding between the mRNA and polypeptide, for example, a derivative of puromycin, which is one of the antibiotics, is used. Puromycin binds to the C terminus of the polypeptide during elongation on the ribosome, and then the polypeptide is dissociated from the ribosome. In the mRNA display, the puromycin derivative binds to the 3' terminus of the mRNA being translated and this puromycin binds to the C terminus of the polypeptide, thereby linking the mRNA and the polypeptide via a covalent bond.

In the ribosome display and mRNA display, cDNA may be synthesized from mRNA in a complex containing the polypeptide that binds to the target polypeptide/protein and the nucleic acid, and amplified by PCR, followed by another transcription and translation reaction. This advantage is a common characteristic among the in vitro display libraries. Accordingly, in the present invention, it is preferred that the in vitro display be used and it is more preferred that the ribosome display be used.

The scale of the library is usually not less than $1\times10^3$, preferably not less than $1\times10^4$, more preferably not less than $1\times10^5$, still more preferably not less than $1\times10^6$.

Subsequently, by bringing the above-mentioned library of fusion proteins into contact with the target substance, a fusion protein which contains a polypeptide sequence that binds to the target substance is selected from the library of fusion proteins and the nucleic acid construct which encodes it is amplified.

In order to select the polypeptide that binds to the target substance, the polypeptide that binds to the target substance need to be screened from a large number of polypeptides which do not bind to the target. This is carried out in accordance with a known method called panning (Coomber (2002) Method Mol. Biol., vol. 178, p. 133-145). The following is a basic protocol of the panning.

(1) Bring a polypeptide library into contact with a target substance.

(2) Removing other polypeptides contained in the library, which do not bind to the target. For instance, the removal can be achieved by washing.

(3) Collecting a polypeptide which is not removed; that is a polypeptide that binds specifically to the target.

(4) Repeating, as required, the operations (1) to (3) multiple times.

Conditions under which the polypeptide library expressed from the display library or the like can be brought into contact with and bound to the target substance are known (WO95/11922, WO93/03172, and WO91/05058) and those skilled in the art can establish those conditions without excessive burdens.

In cases where the target substance is a metal (including a metal salt and metal oxide), a silicon-containing compound or the like, addition of these substances to a sample containing a complex composed of the polypeptide and mRNA allows the contact. Alternatively, the target substance may be bound to a carrier such as a plate, a column or the like; and a sample containing the complex composed of the polypeptide and mRNA may be brought into contact therewith.

In the case of the ribosome display and mRNA display, when a series of the steps is repeated, nucleic acids contained in the complex having the collected polypeptide-nucleic acid are amplified before the step (1).

For instance, mRNA can be amplified by RT-PCR. By RT-PCR, DNA is synthesized using mRNA as a template. DNA is again transcribed into mRNA, which can be used for formation of the complex.

Meanwhile, in the case of the phage display, when a series of the steps is repeated, before the step (1), phages containing the polypeptide sequence of interest are selected and then proliferated, thereby amplifying the nucleic acid construct comprising the polypeptide sequence of interest.

By the above operations, a specific peptide sequence which can impart a target substance binding-ability to a protein of interest or part thereof is concentrated.

Sequence information can be identified by analyzing the sequence of the obtained mRNA.

<Peptide that Binds Specifically to a Metal Oxide and/or a Silicon-containing Compound>

The peptide of the present invention contains the following amino acid sequence.

Tyr-$Xaa^0$-$Xaa^1$-Tyr-Tyr-$Xaa^2$-$Xaa^3$-Tyr-$Xaa^4$-$Xaa^5$-$Xaa^6$-$Xaa^7$-$Xaa^8$-$Xaa^9$-$Xaa^{10}$-$Xaa^{11}$ (SEQ ID NO: 4)

wherein $Xaa^0$, $Xaa^1$, $Xaa^2$, $Xaa^3$, $Xaa^4$, $Xaa^5$, $Xaa^6$, $Xaa^7$, $Xaa^8$, $Xaa^9$, $Xaa^{10}$ and $Xaa^{11}$ represents any amino acid. As long as a binding capacity to a metal oxide and/or a silicon-containing compound is maintained, these amino acids may be either naturally occurring or non-naturally occurring amino acids with naturally occurring amino acids being preferred. These amino acids may be L-type amino acids, and may also be replaced with corresponding D-type amino acids. Peptides having D-type amino acid(s) have advantage in stability of the peptides in a living body. The following is more preferred examples for each amino acid (SEQ ID NO: 21).

It is preferred that $Xaa^0$ be Tyr, Asn or a derivative thereof.

It is preferred that $Xaa^1$ be Asn, Asp, Gly, Arg or a derivative thereof.

It is preferred that $Xaa^2$ be Ser, Tyr, Gly or a derivative thereof.

It is preferred that $Xaa^3$ be Asn, Ser, Gly, Arg, Asp or a derivative thereof.

It is preferred that $Xaa^4$ be Tyr, Asn, Arg or a derivative thereof.

It is preferred that $Xaa^5$ be Gly, Asp, Tyr, Arg or a derivative thereof.

It is preferred that $Xaa^6$ be Arg, Gly, Asp, Asn or a derivative thereof.

It is preferred that $Xaa^7$ be Ser, Asp, Gly, His or a derivative thereof.

It is preferred that $Xaa^8$ be Tyr, Gly or a derivative thereof.

It is preferred that $Xaa^9$ be Ser, Arg, Gly or a derivative thereof.

It is preferred that $Xaa^{10}$ be Ser, Gly, Arg, Asn or a derivative thereof.

It is preferred that $Xaa^{11}$ be Asp, Cys, Arg, Tyr or a derivative thereof.

As the derivatives mentioned above, the following is exemplified.

Examples of the tyrosine derivatives include dihydroxyphenylalanine, phosphotyrosine, and O-methyltyrosine.

An example of the serine derivatives includes phosphoserine.

Examples of the arginine derivatives include hydroxyarginine, monomethylarginine, and dimethylarginine (both symmetric and asymmetric dimethylarginine can be used).

Examples of the cysteine derivatives include S—X—cysteine (X represents alkyl such as methyl, hydroxy and the like), selenocysteine.

An example of the asparagine derivative includes glutamine.

An example of the aspartic acid derivative includes glutamic acid.

An example of the histidine derivative includes 1-methyl histidine.

Concrete examples of the amino acid sequence of SEQ ID NO: 4 include the following amino acid sequence.

```
TOP-1
                                              (SEQ ID NO: 6)
Tyr-Tyr-Asn-Tyr-Tyr-Ser-Asn-Tyr-Tyr-Gly-Arg-Ser-

Tyr-Ser-Ser-Asp

TOP-2
                                              (SEQ ID NO: 8)
Tyr-Tyr-Asp-Tyr-Tyr-Tyr-Ser-Tyr-Asn-Asp-Gly-

Asp-Tyr-Arg-Gly-Cys

TOP-3
                                             (SEQ ID NO: 10)
Tyr-Tyr-Asn-Tyr-Tyr-Tyr-Gly-Tyr-Arg-Tyr-Asp-

Gly-Gly-Arg-Gly-Cys

TOP-4
                                             (SEQ ID NO: 16)
Tyr-Tyr-Gly-Arg-Tyr-Ser-Asp-Tyr-Tyr-Asp-Asn-

Gly-Tyr-Gly-Arg-Arg

TOP-5
                                             (SEQ ID NO: 18)
Tyr-Asn-Arg-Tyr-Asp-Gly-Arg-Tyr-Tyr-Arg-Asp-

His-Gly-Arg-Asn-Tyr
```

The peptide of the present invention may also be one containing the following amino acid sequence.

```
TOP-6
                                             (SEQ ID NO: 20)
Tyr-Asn-Asp-Tyr-Tyr-Tyr-Tyr-Cys-Tyr-Arg-Asp-Tyr-

Asp
```

As long as a binding capacity to a metal oxide or a silicon-containing compound is retained (for example, not less than 80% compared with the capacity before alteration), the sequence may be the same sequence except that 1 or 2 amino acids are substituted, deleted, inserted, or added in SEQ ID NO: 6, 8, 10, 16, 18, or 20.

The above peptide may be artificially synthesized or prepared by a genetic engineering process.

Examples of the metal oxide to which the peptide of the present invention binds include zinc oxide (ZnO), cobalt oxide ($Co_3O_4$), titanium dioxide ($TiO_2$), iron oxide ($Fe_3O_4$) and the like. The peptide of the present invention may be required to bind one or more types of these. Examples of the silicon-containing compound to which the peptide of the present invention binds include an inorganic silicide including silicon oxide such as silicon dioxide ($SiO_2$) or the like, and an organic silicide such as silicone or the like. The peptide of the present invention may be required to bind one or more types of these. The peptide of the present invention may be one that binds to either one of the metal oxide or the silicon-containing compound, or may be one that binds to both of them.

The polynucleotide of the present invention encodes the above peptide. The polynucleotide of the present invention may be any polynucleotide as long as it has a base sequence corresponding to the amino acid sequence of the above peptide and can have a sequence with any codons corresponding to each amino acid being linked. For instance, a polynucleotide encoding the peptide of SEQ ID NO: 6 includes the base sequence of SEQ ID NO: 5, a polynucleotide encoding the peptide of SEQ ID NO: 8 includes the base sequence of SEQ ID NO: 7, a polynucleotide encoding the peptide of SEQ ID NO: 10 includes the base sequence of SEQ ID NO: 9.

In addition, a polynucleotide encoding the peptide of SEQ ID NO: 16 includes the base sequence of SEQ ID NO: 15, a polynucleotide encoding the peptide of SEQ ID NO: 18 includes the base sequence of SEQ ID NO: 17, a polynucleotide encoding the peptide of SEQ ID NO: 20 includes the base sequence of SEQ ID NO: 19.

The vector of the present invention is a vector comprising the above polynucleotide and preferably a vector having a structure in which the above polynucleotide is placed downstream of a promoter sequence so as to enable its expression, and, further downstream thereof, a restriction enzyme recognition site (preferably a multiple cloning site) for incorporating a gene (a gene of interest) encoding the protein of interest or part thereof is placed. In the restriction enzyme recognition site, the gene of interest is linked in flame to the base sequence encoding the peptide of the present invention and, by introducing it into an appropriate host, a fusion protein composed of the peptide of the present invention and the protein of interest or part thereof can be expressed.

The vector of the present invention can be for prokaryotic cells such as *Escherichia coli*, for mammals, viral vector, for yeast, or for a cell free translation system; and units containing a polynucleotide encoding the above promoter sequence and the peptide of the present invention, and the restriction enzyme recognition site can be incorporated into the vector for each host, thereby preparing a vector appropriate to a respective host.

The type of protein linked to the peptide of the present invention is not particularly restricted and any protein can be used. Examples thereof include an enzyme, a receptor, a cell growth factor, a transcription factor, and the like.

Cloning is carried out based on a known sequence or a sequence identified personally, and the resultant is linked in flame with the base sequence encoding the peptide of the present invention in the restriction enzyme recognition site of the vector of the present invention to prepare a recombinant vector, followed by introducing the resulting vector into a host, thereby obtaining a fusion protein. As long as the peptide and the protein of interest or part thereof are linked in flame, any amino acid sequence consisting of 1 to several amino acids (for example 1 to 10 amino acids) may be contained between them. This amino acid sequence can be any sequence as long as it does not inhibit the binding ability of the peptide to a metal oxide and/or a silicon-containing compound and activities of the protein and examples thereof include another peptide tag and a protease recognition sequence.

The fusion protein may be one in which the peptide of the present invention and protein of interest or part thereof are linked through chemical binding, and examples of the mode of the chemical binding include a mode wherein the peptide of the present invention is bound via an amino group at the amino terminus of the protein.

Collection of a fusion protein from host cells can be carried out by using affinity between the peptide of the present invention and a metal oxide or a silicon-containing compound. In cases where the fusion protein is produced and secreted, or in cases where the protein is produced using a cell free translation system, the fusion protein can be specifically adsorbed to be collected by bringing a culture supernatant or a supernatant of the cell free translation system into contact with the metal oxide or the silicon-containing compound. Also, when the fusion protein is generated inside host cells, the protein can be collected from a cell extract obtained by homogenizing the cells. A secretory signal may be added to the fusion protein such that the fusion protein is produced and secreted.

A method of purifying the protein of the present invention is characterized in that a sample containing the above-mentioned fusion protein is brought into contact with the metal oxide or the silicon-containing compound; the fusion protein in the sample is bound to the metal oxide or the silicon-containing compound; and the fusion protein that binds to the metal oxide or the silicon-containing compound is collected. That is, the purification is carried out using the metal oxide or the silicon-containing compound as an affinity carrier.

After the fusion protein is collected, the fusion protein that binds to the metal oxide or the silicon-containing compound is eluted, thereby obtaining a pure fusion protein.

Examples of the sample containing the fusion protein include the culture supernatant and a cell extract described above.

Examples of a method of bringing the sample into contact with the metal oxide or the silicon-containing compound include a method of mixing the sample and fine particles of the metal oxide or the silicon-containing compound in a batch manner, a method of loading the sample onto a column filled with the fine particles of the metal oxide or the silicon-containing compound, and the like. The column can be a spin column so as to be subjected to centrifugation; and can be in a mode wherein the sample containing the fusion protein is extruded through the pointed end of tip bedded with the fine particles of the metal oxide or the silicon-containing compound and passed through the layer of the fine particles of the metal oxide or the silicon-containing compound. When the fine particles of the metal oxide or the silicon-containing compound are used, the particle diameter thereof is arbitrarily selected according to the scale of purification or the like; and it is preferred that one with a diameter of several tens of nm to 10 μm be used. As the fine particle of the metal oxide or the silicon-containing compound, for example, commercially available one can be used.

It is preferred that the fine particles of the metal oxide or the silicon-containing compound be equilibrated with a physiological buffer solution before the contact of the metal oxide or the silicon-containing compound with the sample. The physiological buffer solution can be arbitrarily selected to be used according to properties of the protein, and examples thereof include a phosphate buffer, Tris buffer and the like.

In addition, in order to suppress non-specific adsorption it is preferred that blocking be carried out after the equilibration. As for a blocking solution, a known one such as bovine serum albumin or the like can be used.

The contact of the sample with the metal oxide or the silicon-containing compound may be taken place at room temperature and preferably at low temperatures to avoid loss of activities of the protein.

After the contact of the sample with the metal oxide or the silicon-containing compound, washing is carried out using a washing solution containing a low concentration of a detergent or the like and then the bound fusion protein is eluted.

As an elution solution, an aqueous solution with a high concentration of a salt or the like can, for example, be used.

A kit of the present invention is a kit for expressing and purifying a protein, which kit contains fine particles of a metal oxide or a silicon-containing compound and a vector comprising a polynucleotide encoding the peptide of the present invention described above. It may contain a spin column or a purification column filled with the fine particles of the metal oxide or the silicon-containing compound. The kit of the present invention may be one containing an elution solution, a washing solution, an equilibration solution, a blocking solution or the like.

A method of immobilizing the protein of the present invention is characterized in that the above fusion protein is immobilized onto a substrate via a metal oxide or a silicon-containing compound, wherein at least the surface of the substrate is composed of the metal oxide or the silicon-containing compound. The fusion protein can be immobilized onto the surface of the substrate by interactions between the metal oxide or the silicon-containing compound on the surface of the substrate and the peptide contained in the fusion protein. The substrate is not particularly restricted as long as the surface thereof can be adhered with the metal oxide or the silicon-containing compound, and examples thereof include a glass plate, a plastic plate, a silicone plate, glass beads, plastic beads, silicone beads and the like. It is preferred that the adhesion of the metal oxide or the silicon-containing compound to the surface of the plate or the beads be by physical adsorption. The metal oxide or the silicon-containing compound may be the substrate by itself. According to a method of immobilizing the protein of the present invention, a protein chip in which one or more proteins are immobilized via the peptide sequence of the present invention can be obtained and such a protein chip can be suitably used for analyzing interactions between proteins or the like.

An antibody of the present invention is an antibody against the peptide of the present invention.

As long as the antibody specifically recognizes the peptide of the present invention, it may be a polyclonal antibody or a monoclonal antibody.

The polyclonal antibody can be obtained by, for example, immunizing a non-human mammal such as a mouse or a rabbit with an immunogen containing the peptide of the present invention; and, from the resulting antiserum, collecting an antibody recognizing specifically the peptide of the present invention. The immunogen may be bound to a carrier protein such as BSA, KLH or the like and used in the immunization. The antibody can be purified with protein A or the like.

The monoclonal antibody can be obtained by, for example, immunizing a non-human mammal such as a mouse or the like with an immunogen containing the peptide of the present invention, fusing lymphocytes isolated from the mammal with mouse myeloma cells to prepare hybridoma, selecting an antibody recognizing specifically the peptide of the present invention from antibodies produced by the obtained hybridoma. The monoclonal antibody includes a fragment of the monoclonal antibody such as F(ab')$_2$ fragment antibody, F(ab') fragment antibody, short chain antibody (scFv), diabodies, minibodies or the like.

The antibody of the present invention can be used in detection, immunoprecipitation, FACS, ELISA or the like for the fusion protein which comprises the peptide of the present invention.

A fusion protein of the peptide of the present invention can be used as a surface treatment agent for biomaterials containing the metal oxide or the silicon-containing compound. By adding the fusion protein to the surface of the biomaterials, the fusion protein can be bound to the surface of the biomaterials, thereby imparting a characteristic of the protein to the surface of the biomaterial. The biomaterial may be a material made up of the metal oxide or the silicon-containing compound itself, or a material in which the metal oxide or the silicon-containing compound is coated on the surface of a substrate such as metal, plastic, silicone or the like. Examples of the biomaterial include artificial joint, artificial epiphysis, artificial valve, implantable artificial heart, cardiac pacemaker parts, artificial dental root, denture base, wire for correction, crown, bone fracture fixation material, spinal fixation device, spine spacer, stent, surgical instrument such as scalpel, catheter, contact lens, and the like.

The biomaterial may be subjected to ex vivo surface treatment with the fusion protein before being introduced into a living body. Or the biomaterial which has been already introduced in the living body may be subjected to surface treatment inside the living body using the fusion protein delivered from the outside of the body.

In cases where the fusion protein is a fusion protein composed of the above-mentioned peptide and a cell growth factor, by modifying the surface of a biomaterial containing a metal oxide or a silicon dioxide using this fusion protein, cell functions can be induced onto the biomaterial, which is thus useful as a pharmaceutical for regenerative medicine. And induction of stem cell differentiation is also benefited.

For example, in cases where a cell growth factor is EGF or a fibroblast growth factor (FGF), biofunctions of keratinocytes, fibroblasts or the like can be induced onto the biomaterial modified with this, which is thus useful in wound treatment, angiogenesis of a skull defective part or heart coronary artery, or the like.

Also, in cases where the cell growth factor is a bone morphogenetic factor (BMP), biofunctions of osteoblast cells can be induced onto the biomaterial modified with this, which is thus useful in cartilage regeneration or bone fracture treatment.

Additionally, in cases where the cell growth factor is a tumor necrosis factor (TNF α), apoptosis of cells adhered onto the biomaterials modified with this can be induced, which is thus useful in prevention of recurrent stenosis of the blood vessel around a metallic material (such as a stent) which is introduced in surgical procedure related to the circulatory organ and/or blood vessel represented by myocardial infarction.

In addition, in cases where the cell growth factor is a nerve growth factor (NGF), biofunctions of nerve cells can be induced onto the biomaterial modified with this, which is thus useful in treatment of brain damage by regeneration of the nerve or treatment of cranial nerve diseases such as Alzheimer's disease, improvement of motor neuropathy or peripheral neuropathy, recovery from glaucoma or the like.

By using the peptide of the present invention, a biologically active substance such as a biologically active peptide (including a cyclic peptide as well), a nucleic acid, a biologically active compound, a sugar chain or the like can be immobilized onto a substrate. That is, by binding chemically the biologically active substance such as the biologically active peptide, the nucleic acid, the biologically active compound, the sugar chain or the like to the peptide of the present invention; and by bringing the resultant into contact with the substrate at least whose surface is composed of the metal oxide or the silicon-containing compound, these substances can be immobilized onto the substrate via the peptide of the present invention.

In this case, when the biologically active substance is, for example, cyclosporin A, which is a cyclic polypeptide, immunosuppressive effects around an affected area and/or local immunosuppressive effects can be expected by slow release from the biomaterial whose surface is modified with this, which is thus beneficial in a immunosuppressive therapy with small side effects. Also, it is useful to suppress rejection in liver transplantation, kidney transplantation or bone marrow transplantation.

EXAMPLES

The present invention will be more concretely described by reference to the examples below. The present invention is, however, not limited to the modes below.

Example 1

Development of Novel Ribosome Display Method of Creating "Metal Binding Peptide Aptamer Fusion EGF" and Novel Selection of "TiO$_2$ Binding Peptide Aptamer"

A novel ribosome display method (FIG. 1) developed this time is mainly composed of five steps.

(1) An artificial sequence in which a part of the sequence of primer 2 below [24 to 47 in SEQ ID NO: 12], the SD sequence, a start codon, SfiI restriction enzyme site (1), SfiI restriction enzyme site (2), the EGF sequence, a Ps sequence, the SecM stall sequence are placed in the order mentioned is constructed in a cloning site of a commercially available plasmid (the entire sequence of the construct is shown in SEQ ID NO: 13). Subsequently, a DNA library (FIG. 1-1) encoding the sequence information of an artificial peptide library is chemically synthesized; and, after both of termini of each of DNAs are digested with SfiI, is inserted between the SfiI restriction enzyme site (1) and SfiI restriction enzyme site (2) in the plasmid (FIG. 2-1: the sequence of the obtained construct is shown in SEQ ID NO: 1). A characteristic of this DNA library is to be composed of 16 NRY codons (N=A, G, C, T; R=A, G; Y=C, T) (FIG. 2-1). Because of this, in a translation process, a linear peptide library composed of 16 amino acids in which eight types of amino acids (Tyr, Cys, His, Arg, Asn, Ser, Asp, Gly) are randomly appeared can be synthesized. Next, with the plasmid into which the DNA library is introduced as a template, a linear DNA template is prepared by PCR using primer 1 [5'-aaacagctatgaccatgatta-3': SEQ ID NO: 11] and primer 2 [5'-ttaatacgactcactatagaaaagtcgacaataattttgtttaactt-3': SEQ ID NO: 12] (the underlined portion of the sequence of primer 2=T7 promoter) as well as Ex-Taq (manufactured by Takara).

(2) A mRNA library is prepared by in vitro transcription using the T7 promoter (FIG. 2-1) of the DNA template (FIG. 1-2).

(3) An "artificial peptide library (APL)-epidermal growth factor (EGF)-mRNA-ribosome complex" is prepared by in vitro translation by using a cell-free protein translation system (PURESYSTEM classic II manufactured by BioComber Co., Ltd.) (FIG. 1-3).

Innovative ideas to attain preparation and stabilization of this complex are, in the DNA template, to introduce the EGF and a protein spacer (Ps) having SecM stall sequences in its C terminus downstream of APL and to completely remove a stop codon (FIG. 2-1).

Here, the "APL fusion EGF" itself is employed as a library by fusing EGF to the C terminus of a peptide aptamer that binds to TiO$_2$, and a selection operation is carried out using a binding activity to TiO$_2$ as an index. By this, the selected peptide aptamer has, even in its state fusing with EGF, tremendously increased provability of retaining the TiO$_2$-binding ability. This is thus the innovative idea to avoid "deactivation of target-binding ability of the peptide aptamer", which deactivation takes place in cases where a peptide aptamer is selected alone and then fused to EGF. The Ps is, in an intracellular protein Bcl-xL, a sequence extracted uniquely from a region whose degrees of freedom is too high to be identified by X-ray crystallography, and a novel sequence into which Gly is appropriately introduced for having higher flexibility. (In a development process of the present technique, it was revealed that efficiency of expression of EGF fused with this sequence was/is higher than that of EGF fused with other protein spacer. Thus, it is one of the important factors to carry out preparation of the ribosome complex more efficiently.) The SecM stall sequence plays a role in stably immobilizing an APL-EGF-Ps part on the ribosome by binding to the inside of a tunnel of the ribosome concurrently with translation. In addition, the removal of the stop codon inhibits recognition of mRNA by dissociation factors and thus enables the ribosome presenting APL-EGF-Ps to be retained on mRNA for a long period of time, which allows preparation of more stable complexes.

(4) The "artificial peptide library (APL)-epidermal growth factor (EGF)-mRNA-ribosome complex" (an in vitro translation solution is used as is) and $TiO_2$ particles (manufactured by Kanto Chemical Co., Inc.) (about 0.2 mg) as a target metal are mixed and stirred for about 1 hour at 4° C. Then, after washing with TBS-T buffer (pH 7.5), only complexes displaying special peptides which specifically bind to surface structures of the $TiO_2$ are selected (FIG. 1-4).

(5) The thus selected complex is degraded by being reacted with an EDTA solution, and mRNA is collected by a column (manufactured by Qiagen) (FIG. 1-5). And using the collected RNA as a template, a reverse transcription (RT) reaction (a total amount of 200 ml) was carried out (RNA: 100 ml, primer 1 [SEQ ID NO: 11]: 40 pmol, dNTPs: 100 nmol, RNasin 2 ml (manufactured by Promega), PrimeScript Reverse Transcriptase: 8 ml (manufactured by TaKaRa)). Subsequently, using the RT product as a source, PCR (RT product: 200 ml, primer 1 [SEQ ID NO: 11]: 200 pmol, primer 2 [SEQ ID NO: 12]: 200 pmol, dNTPs: 200 nmol, PrimeSTAR GXL DNA polymerase: 20 ml (manufactured by TaKaRa)) (a total amount of 1000 ml) is carried out, thereby constructing a DNA template necessary for a next selection experiment.

Furthermore, after repeating the cycle operation shown in FIG. 1 five (5) times, the amino acid sequences (25 amino acid sequences) recorded by the mRNA were analyzed and, as a result, the presence of 3 kinds of peptides (TOP1, TOP2, and TOP3) having an overlapping sequence could be confirmed (Table 1). In any of the peptides, a characteristic sequence with many tyrosines was observed and the peptides were non-naturally occurring novel peptides. In addition, it was also found that the peptides had a completely different sequence from that of a $TiO_2$ binding peptide TBP-1 (Table 1), which was previously selected by a phage display method.

TABLE 1

(SEQ ID NOS 6, 8, 10, and 22, respectively, in order of appearance)

| Clone | Sequence | Freq. |
|---|---|---|
| TOP1 | Y Y N Y Y S N Y Y G R S Y S S D | 6/25 |
| TOP2 | Y Y D Y Y Y S Y N D G D Y R G C | 5/25 |
| TOP3 | Y Y N Y Y Y G Y R Y D G G R G C | 2/25 |
| TBP-1 | R K L P D A P G M H T W | |

Freq. indicates an appearance frequency in the 25 obtained clones.
TBP-1 shows a peptide reported in Non-patent Documents 6 and 7.

In addition, from the same experiment, the following three types of $TiO_2$ binding peptides were further obtained.

(SEQ ID NO: 16)
TOP4 Y Y G R Y S D Y Y D N G Y G R R (SEQ ID NO: 18)
TOP5 Y N R Y D G R Y Y R D H G R N Y (SEQ ID NO: 20)
TOP6 Y N D Y Y Y Y C Y R D Y D

Example 2

Creation of Various "Peptide Fusion EGFs" and Evaluation of Their $TiO_2$-binding Ability and $SiO_2$-binding Ability Here, DNA templates for expressing P-EGFs which are novel proteins of EGF with various peptides being fused (FIG. 3-1; TOP1-EGF [EGF with a novel peptide TOP1 sequence selected this time at its N terminus and added with a FLAG tag for detection to its C terminus], H6-EGF ('H6' disclosed as SEQ ID NO: 23) [EGF with a sequence of six His residues (SEQ ID NO: 23) being tandemly placed at its N terminus and added with the FLAG tag for detection to its C terminus], TBP-EGF [EGF with a sequence of $TiO_2$ binding peptide minTBP-1 selected by a phage display method (an essential sequence for exhibiting a $TiO_2$-binding ability of TBP-1) at its N terminus and added with the FLAG tag for detection to its C terminus]) were newly constructed; and they were expressed by a cell-free protein translation system (PURESYSTEM classic II manufactured by BioComber Co., Ltd.).

And then, in western blot following electrophoresis of a translation solution (7 μl each) of various P-EGFs, a respective band (9.5 to 10 kDa) was confirmed at a position where each P-EGF was supposed to be observed (FIG. 3-2). Furthermore, from comparison of their luminescence intensity, it could be also confirmed that P-EGFs were expressed at compatible levels. (Here, the P-EGF band was, after recognized by an anti-FLAG antibody HRP complex, detected by a luminescent phenomenon derived from a reaction of a chemiluminescence reagent with HRP.)

Subsequently, in accordance with a scheme in the left in FIG. 4-1, various P-EGF solutions (a 10 μl solution of P-EGF translated using PURESYSTEM classic II manufactured by BioComber Co., Ltd.) and $TiO_2$ particles (manufactured by Kanto Chemical Co., Inc.) are mixed. After centrifugal precipitation and a washing operation (TBS-T buffer, pH 7.5) were repeated 4 times, only proteins bound to the surface of the particles were subjected to electrophoresis. And only for TOP1-EGF, a luminescent band could be observed at a position where it is supposed to be observed in the western blot (the right in FIG. 4-1, the P-EGF band was, after recognized by an anti-FLAG antibody HRP complex, detected by a luminescent phenomenon derived from a reaction of a chemiluminescence reagent with HRP). This revealed that TOP1 strongly exhibited the $TiO_2$-binding ability. In addition, a band for TBP-EGF selected by a phage display method was not detected, which could thus prove a high $TiO_2$-binding ability of TOP1 selected by this novel technique and superiority of the novel ribosome display method as a peptide aptamer selection method.

Subsequently, in accordance with a scheme in the left in FIG. 4-2, various P-EGF solutions (about 2.0 ng, 10 μl in TBS, pH 7.5) were added on a $TiO_2$ plate (a plate produced by vapor deposition of titanium on the surface of a glass plate with a diameter of 15 mm and a thickness of 0.6 mm (manufactured by Matsunami Glass Ind., Ltd.) (the vapor deposition step was requested to Osaka Vacuum Industrial Co., Ltd.) was used); and a washing operation (TBS-T buffer, pH 7.5) was repeated 3 times. And, after blocking with 0.1% BSA solution, an anti-human EGF antibody was added as a primary antibody. Furthermore, after the washing operation (TBS-T buffer, pH 7.5) was repeated 3 times, an anti-mouse IgG antibody HRP conjugate was added as a secondary antibody. At the end, using a luminescent phenomenon by a reaction between a chemiluminescence reagent and HRP as an index, the presence of protein immobilized on the TiO$_2$ plate was detected. As a result, only for the TiO$_2$ plate to which TOP1-EGF was added, the luminescent phenomenon could be observed (the right in FIG. 4-2). This revealed that TOP1-EGF spontaneously and strongly bound to the TiO$_2$ plate as well. In addition, because EGF to which a peptide was not fused did not exhibit TiO$_2$ binding by itself, it was revealed that TOP1-EGF was immobilized on the TiO$_2$ plate, not by a non-specific binding, but by the specific binding ability of TOP1.

Furthermore, in order to find out further possibilities of metal binding ability of TOP1, a binding ability against SiO$_2$, which was a major component of glass, was evaluated. This was because the surface structure of SiO$_2$ was known to be very similar to that of TiO$_2$ and TOP1-EGF was thus expected to have the SiO$_2$-binding ability. In view of this, in accordance with a scheme in the left in FIG. 5, various P-EGF solutions (about 2.0 ng, 10 μl in TBS, pH 7.5) were added on a SiO$_2$ plate (a glass plate with a diameter of 15 mm and a thickness of 0.6 mm (manufactured by Matsunami Glass Ind., Ltd.)), and a washing operation (TBS-T buffer, pH 7.5) was repeated 3 times. And, after blocking with 0.1% BSA solution, an anti-human EGF antibody was added as a primary antibody. Furthermore, after the washing operation (TBS-T buffer, pH 7.5) was repeated 3 times, an anti-mouse IgG antibody HRP complex was added as a secondary antibody. At the end, using a luminescent phenomenon by a reaction between a chemiluminescence reagent and HRP as an index, the presence of protein immobilized on the SiO$_2$ plate was detected. As a result, only for the SiO$_2$ plate to which TOP1-EGF was added, the luminescent phenomenon could be observed (the right in FIG. 5). This revealed that TOP1-EGF spontaneously and strongly bound to the SiO$_2$ plate as well. It was hence found that TOP1 was a novel peptide aptamer having both of TiO$_2$-binding ability and SiO$_2$-binding ability.

Example 3

Evaluation of Cell Proliferation Activity of "TiO$_2$ Binding Peptide Aptamer Fusion EGF" on TiO$_2$ Plate An experiment was here carried out in order to prove TOP1-EGF immobilized on a TiO$_2$ plate was capable of exhibiting a function of inducing proliferation of various cells.

First, in accordance with a scheme in the left in FIG. 6-1, a TOP 1-EGF solution (about 5.0 ng, 12 μl in TBS, pH 7.5) was added onto the TiO$_2$ plate and a washing operation (TBS-T buffer, pH 7.5) was then repeated 3 times, followed by blocking with 0.1% BSA solution, thereby producing a "TOP1-EGF immobilized TiO$_2$ plate." Then, about 5,000 keratinocytes were seeded on the TOP1-EGF immobilized TiO$_2$ plate, cultured for 6 days (1% FBS containing DMEM medium was used), and subjected to microscopy (cells were stained in purple). As a result, the keratinocytes on the TOP1-EGF immobilized TiO$_2$ plate markedly proliferated as compared with ones on a TiO$_2$ plate on which TOP1-EGF was not immobilized, and the state of a large amount of keratins being produced around those cells was observed (FIG. 6-1 right). Thus, it was revealed that TOP1-EGF not only bound spontaneously onto the TiO$_2$ plate but also induced proliferation of keratinocytes, which proliferation is vital to formation of the skin.

Furthermore, by an operation similar to a scheme in the left in FIG. 6-2 and the above, the "TOP1-EGF immobilized TiO$_2$ plate" was produced. About 5,000 NIH3T3 fibroblasts were seeded on the TOP1-EGF immobilized TiO$_2$ plate, cultured for 6 days (1% FBS containing DMEM medium was used), and subjected to microscopy (cells were stained in purple). As a result, when compared with ones on a TiO$_2$ plate on which TOP1-EGF was not immobilized, NIH3T3 cells on the TOP1-EGF immobilized TiO$_2$ plate markedly proliferated and the state of each cell growing and widely extending was observed (the right in FIG. 6-2). It was thus revealed that TOP1-EGF not only bound to spontaneously onto the TiO$_2$ plate but also induced proliferation of the fibroblasts.

Example 4

Evaluation of TiO$_2$-binding Ability of Chemically Synthesized "TiO$_2$ Binding Peptide Aptamer Fusion EGF" and Evaluation of its Cell Proliferation Activity on TiO$_2$ Plate Conventionally, an *Escherichia coli* expression system and cell-free protein translation system are primarily employed for protein synthesis. In the former, namely the *Escherichia coli* expression system, even though operations of culturing, homogenizing and extraction, and purification treatment are time consuming, the system is able to synthesize a large amount of proteins and is thus most widely used. Yet, burden and toxicity to *Escherichia coli* caused by the expression of proteins are problematic, and there are many cases where a protein of interest cannot be obtained. On the other hand, the latter, namely the cell-free protein translation system is convenient in that expression and treatment can be carried out in a short period of time. Yet, synthesis of a large amount of proteins is difficult. Besides, it costs high, which is always problematic. Hence, a large amount of proteins can be obtained in a short period of time and at a low price on condition that the proteins can be synthesized by a chemical technique. In view of this, it was this time attempted to chemically synthesize TOP1-EGF by a peptide solid phase method. Conventionally, it has been considered to be very difficult for the solid phase method to synthesize a peptide with more than 40 to 50 amino acids in length. However, sTOP1-EGF composed of 80 amino acids (MQAYYNYYSNYYGRSYSS-DGQLGQFEGNSDSECPLSHDGYCLHDGVCMYI EALDKYACNCVVGYIGERCQYRDLKWWELR: SEQ ID NO: 14) was successfully synthesized this time. With that, TiO$_2$-binding ability of this sTOP1-EGF and cell proliferation activity on TiO$_2$ plate were evaluated.

First, in accordance with a scheme in the left in FIG. 7-1, various P-EGF solutions (about 2.0 ng, 10 μl in TBS, pH 7.5) were added on a TiO$_2$ plate and a washing operation (TBS-T buffer, pH 7.5) was repeated 3 times. And, after blocking with 0.1% BSA solution, an anti-human EGF antibody was added as a primary antibody. Furthermore, after the washing operation (TBS-T buffer, pH 7.5) was repeated 3 times, an anti-mouse IgG antibody HRP complex was added as a secondary antibody. At the end, using a luminescent phenomenon by a reaction between a chemiluminescence reagent and HRP as an index, the presence of protein immobilized on the TiO$_2$ plate was detected. As a result, only for the TiO$_2$ plate of a region where sTOP1-EGF was added, the luminescent phenomenon could be confirmed (the right in FIG. 7-1). This revealed that the TiO$_2$-binding ability was retained also in the chemically synthesized sTOP1-EGF.

Furthermore, an experiment to check if sTOP1-EGF immobilized on the TiO$_2$ plate exhibited a function of inducing cell proliferation was carried out. First, in accordance with a scheme in the left in FIG. 7-2, sTOP1-EGF solution (about 5.0 ng, 12 μl in TBS, pH 7.5) was added onto the $TiO_2$ plate and a washing operation (TBS-T buffer, pH 7.5) was then repeated 3 times. And, by blocking with 0.1% BSA solution, a "sTOP1-EGF immobilized $TiO_2$ plate" was prepared. And then, ca. 5,000 NRK-49F fibroblasts were seeded on the sTOP1-EGF immobilized $TiO_2$ plate, cultured for 6 days (1% FBS containing DMEM medium was used), and subjected to microscopy (cells were not stained). As a result, when compared with ones on a $TiO_2$ plate on which EGF alone was added, NRK-49F fibroblasts on the sTOP1-EGF immobilized $TiO_2$ plate markedly proliferated and the state of the cells maintaining active life actions was observed (the right in FIG. 7-2). It was therefore revealed that the chemically synthesized sTOP1-EGF not only bound onto the $TiO_2$ plate spontaneously but also had an activity of inducing proliferation of the fibroblasts.

Industrial Applicability

A method of the present invention of selecting polypeptide sequence which imparts a protein of interest a target substance binding-ability is useful in the fields of genetic engineering, peptide engineering and the like.

In addition, the peptide of the present invention is useful not only for research purposes but also in the field of medicine such as medical transplantation, regenerative medicine or the like.

While the invention has been described in detail with reference to preferred embodiments thereof, it will be apparent to one skilled in the art that various changes can be made, and equivalents employed, without departing from the scope of the invention. Each of the aforementioned documents, including the foreign priority document, JP 2010-054927, is incorporated by reference herein in its entirety.

What is claimed is:

1. A peptide comprising any one of the following amino acid sequences:

Tyr-Tyr-Asn-Tyr-Tyr-Ser-Asn-Tyr-Tyr-Gly-Arg-Ser-Tyr-Ser-Ser-Asp (SEQ ID NO: 6);

Tyr-Tyr-Asp-Tyr-Tyr-Tyr-Ser-Tyr-Asn-Asp-Gly-Asp-Tyr-Arg-Gly-Cys (SEQ ID NO: 8);

Tyr-Tyr-Asn-Tyr-Tyr-Tyr-Gly-Tyr-Arg-Tyr-Asp-Gly-Gly-Arg-Gly-Cys (SEQ ID NO: 10);

Tyr-Tyr-Gly-Arg-Tyr-Ser-Asp-Tyr-Tyr-Asp-Asn-Gly-Tyr-Gly-Arg-Arg (SEQ ID NO: 16); or

Tyr-Asn-Arg-Tyr-Asp-Gly-Arg-Tyr-Tyr-Arg-Asp-His-Gly-Arg-Asn-Tyr (SEQ ID NO: 18);

wherein up to two amino acids selected from the second, third, sixth, seventh, ninth, tenth, eleventh, twelfth, thirteenth, fourteenth, fifteenth and sixteenth amino acids of each amino acid sequence may contain derivatives of the corresponding amino acids, and wherein the se peptide is capable of binding to a metal oxide or a silicon-containing compound.

2. The peptide according to claim 1 comprising an amino acid sequence selected from the group consisting of SEQ ID NOs: 6, 8, 10, 16 and 18.

3. A peptide comprising the amino acid sequence of SEQ ID NO: 20.

4. A peptide comprising the amino acid sequence of SEQ ID NOs: 6, 8, 10, 16, 18 or 20 including substitution, deletion, insertion, or addition of 1 or 2 amino acids; and being capable of binding to a metal oxide or a silicon-containing compound.

5. A fusion protein comprising the peptide according to claim 1 and a protein or part thereof linked to the peptide.

6. The fusion protein according to claim 5, wherein the protein is a cell growth factor.

7. The fusion protein according to claim 6, wherein the cell growth factor is an epidermal growth factor.

8. A polynucleotide encoding the peptide according to claim 1.

9. A vector comprising the polynucleotide according to claim 8.

10. A method of immobilizing a protein comprising immobilizing the fusion protein according to claim 5 on a substrate, wherein at least the surface of the substrate is composed of a metal oxide or a silicon-containing compound and the protein is immobilized via the metal oxide or the silicon-containing compound.

11. A method of immobilizing a bioactive substance comprising immobilizing a bioactive substance via a metal oxide or a silicon-containing compound by contacting a bioactive substance bound to the peptide according to claim 1 on a substrate at least the surface of which is composed of the metal oxide or the silicon-containing compound.

12. A surface treatment agent for a biomaterial containing a metal oxide or a silicon-containing compound, the surface treatment agent comprising a bioactive substance bound to the peptide according to claim 1.

13. A biomaterial wherein a bioactive substance bound to the peptide according to claim 1 has been immobilized on a substrate at least the surface of which is composed of a metal oxide or a silicon-containing compound.

14. A pharmaceutical comprising a biomaterial wherein a bioactive substance bound to the peptide according to claim 1 has been immobilized on a substrate at least the surface of which is composed of a metal oxide or a silicon-containing compound, which pharmaceutical is used in regenerative medicine by inducing a cell onto the biomaterial.

15. A polynucleotide encoding the fusion protein according to claim 5.

16. A vector comprising the polynucleotide according to claim 15.

17. A surface treatment agent for a biomaterial containing a metal oxide or a silicon-containing compound, the surface treatment agent comprising a bioactive substance bound to the fusion protein according to claim 5.

18. A biomaterial wherein a bioactive substance bound to the fusion protein according to claim 5 has been immobilized on a substrate at least the surface of which is composed of a metal oxide or a silicon-containing compound.

19. A pharmaceutical comprising a biomaterial wherein a bioactive substance bound to the fusion protein according to claim 6 has been immobilized on a substrate at least the surface of which is composed of a metal oxide or a silicon-containing compound, which pharmaceutical is used in regenerative medicine by inducing a cell onto the biomaterial.

20. A polynucleotide encoding the peptide according to claim 4.

21. A method of immobilizing a bioactive substance comprising immobilizing a bioactive substance via a metal oxide or a silicon-containing compound by contacting a bioactive substance bound to the peptide according to claim 4 on a substrate at least the surface of which is composed of the metal oxide or the silicon-containing compound.

* * * * *

UNITED STATES PATENT AND TRADEMARK OFFICE
CERTIFICATE OF CORRECTION

PATENT NO. : 8,697,655 B2
APPLICATION NO. : 13/608052
DATED : April 15, 2014
INVENTOR(S) : A. Wada et al.

It is certified that error appears in the above-identified patent and that said Letters Patent is hereby corrected as shown below:

In the Claims

At column 40, line 56, (claim 1, line 18) of the printed patent, please delete "se" before peptide.

Signed and Sealed this
Sixth Day of January, 2015

Michelle K. Lee
*Deputy Director of the United States Patent and Trademark Office*